(12) United States Patent
Driver et al.

(10) Patent No.: US 9,006,305 B2
(45) Date of Patent: Apr. 14, 2015

(54) BIOCOMPATIBLE MATERIAL

(75) Inventors: Michael Driver, Basingstoke (GB); Brian Tarbit, Ashington (GB); Alexander Gehre, Basingstoke (GB)

(73) Assignee: Vertellus Specialties Inc., Indianapolis, IN (US)

( * ) Notice: Subject to any disclaimer, the term of this patent is extended or adjusted under 35 U.S.C. 154(b) by 300 days.

(21) Appl. No.: 13/601,123

(22) Filed: Aug. 31, 2012

(65) Prior Publication Data

US 2013/0059970 A1    Mar. 7, 2013

Related U.S. Application Data

(60) Provisional application No. 61/530,120, filed on Sep. 1, 2011, provisional application No. 61/558,066, filed on Nov. 10, 2011.

(51) Int. Cl.
| | |
|---|---|
| C08F 2/50 | (2006.01) |
| C08F 2/46 | (2006.01) |
| B29C 71/04 | (2006.01) |
| A61L 2/08 | (2006.01) |
| A61L 24/00 | (2006.01) |
| C08G 61/04 | (2006.01) |
| C07F 9/572 | (2006.01) |
| C08F 30/02 | (2006.01) |
| C07F 9/09 | (2006.01) |
| G02B 1/04 | (2006.01) |
| C08F 230/08 | (2006.01) |

(52) U.S. Cl.
CPC .............. *C07F 9/5722* (2013.01); *C08F 30/02* (2013.01); *C07F 9/091* (2013.01); *G02B 1/043* (2013.01); *C08F 230/08* (2013.01)

(58) Field of Classification Search
CPC combination set(s) only.
See application file for complete search history.

(56) References Cited

U.S. PATENT DOCUMENTS

| | | |
|---|---|---|
| 3,808,178 A | 4/1974 | Gaylord |
| 4,120,570 A | 10/1978 | Gaylord |
| 4,136,250 A | 1/1979 | Mueller et al. |
| 4,153,641 A | 5/1979 | Deichert et al. |
| 4,417,066 A | 11/1983 | Westall |
| 4,740,533 A | 4/1988 | Su et al. |
| 5,034,461 A | 7/1991 | Lai et al. |
| 5,070,215 A | 12/1991 | Bambury et al. |
| 5,270,415 A | 12/1993 | Sulc et al. |
| 5,648,442 A | 7/1997 | Bowers et al. |
| 6,090,901 A | 7/2000 | Bowers et al. |
| 6,200,626 B1 | 3/2001 | Grobe, III et al. |
| 6,743,878 B2 | 6/2004 | Bowers et al. |
| 6,767,979 B1 | 7/2004 | Muir et al. |
| 6,780,930 B2 | 8/2004 | Lewis et al. |
| 6,828,029 B1 | 12/2004 | Lewis et al. |
| 7,268,198 B2 | 9/2007 | Kunzler et al. |
| 7,540,609 B2 | 6/2009 | Chen et al. |
| 2002/0165324 A1 | 11/2002 | Bowers et al. |
| 2003/0152786 A1 | 8/2003 | Lewis et al. |
| 2004/0208985 A1 | 10/2004 | Rowan et al. |
| 2004/0256232 A1 | 12/2004 | Jiang et al. |
| 2006/0012751 A1 | 1/2006 | Rosenzweig et al. |
| 2007/0099868 A1 | 5/2007 | Harats et al. |
| 2007/0296914 A1 | 12/2007 | Hong et al. |
| 2009/0130295 A1 | 5/2009 | Broguiere et al. |
| 2009/0304770 A1 | 12/2009 | Lewis et al. |
| 2010/0048515 A1 | 2/2010 | Harats et al. |
| 2011/0319583 A1 | 12/2011 | Matsuoka et al. |

FOREIGN PATENT DOCUMENTS

| | | |
|---|---|---|
| DE | 1211156 | 2/1966 |
| EP | 0090539 | 11/1981 |
| EP | 0 537 972 | 4/1993 |
| EP | 0580435 | 1/1994 |
| EP | 0767212 | 4/1997 |
| EP | 0730599 | 4/2000 |
| EP | 1122258 | 8/2001 |
| EP | 2 407 493 | 1/2012 |
| JP | 62042995 | * 2/1987 |
| JP | 7 072430 | 3/1995 |
| JP | 1997-291220 | 11/1997 |
| JP | 2000169526 | 6/2000 |
| JP | 2000-186117 | 7/2000 |
| JP | 2007-09060 | 1/2007 |
| JP | 2007009060 | 1/2007 |
| JP | 2012 048224 | 3/2012 |
| WO | WO 92/07885 | 5/1992 |
| WO | WO 96/31566 | 10/1996 |
| WO | WO 2010055914 | 5/2010 |
| WO | WO 2010104000 | 9/2010 |
| WO | WO 2010/147779 | 12/2010 |
| WO | WO 2012/045080 | 4/2012 |
| WO | WO 2012/104349 | 8/2012 |

OTHER PUBLICATIONS

Thomson Scientific, London, GB; AN 2007-180957, XP002686152, & JP 2007 009060 A (Nippon Oils & Fats Co Ltd) Jan. 18, 2007. (Abstract Only).

Lewis A L et al: "Crosslinkable coatings from phosphorylcholine-based polymers", Biomaterials, Elsevier Science Publishers BV., Barking, GB, vol. 22, No. 2, Jan. 15, 2001, pp. 99-111, XPO04236384.

Koinuma, Yasumi et al: "Diester monomer, its polymer, watercontaining soft contact", 1994, XP002687478. (Abstract Only).

Suzuki, Hiroshi et al: "Preparation of polymerizable phosphorylcholine derivatives with medical applications", 1995, XP002687479. (Abstract Only).

Nakabayashi, Nobuo et al: "Low-toxicity aqueous solution of phosphorylcholine group-bearing polymer and its manufacture", 1996, XP002687480. (Abstract Only).

(Continued)

*Primary Examiner* — Ling Choi
*Assistant Examiner* — Jessica E Whiteley
(74) *Attorney, Agent, or Firm* — Barnes & Thornburg LLP

(57) ABSTRACT

Monomers of formula (I) which include a vinyl group, polymers and articles, such as contact lenses, made therefrom, all of which are biocompatible, are described.

16 Claims, No Drawings

(56) References Cited

OTHER PUBLICATIONS

Harats, Dror et al: "Oxidized lipids and uses thereof in the treatment of inflammatory diseases and disorders", 2010, XP002687481. (Abstract Only).

Harats, Dror et al: "Oxidized lipids and uses thereof in the treatment of inflammatory diseases and disorders", 2007, XP002687482. (Abstract Only).

Ol'dekop, Y: "XRN 3984136", XP55044654,accession No. XRN 3984136 Database accession No. XRN 3984136 ; & Y Ol'dekop: "REAXYS XRN=3984136", Zhurnal Organicheskoi Khimii, vol. 15, No. 1, Jan. 1, 1979, pp. 39-50, XP055044654.

Raghavan S et al: "A novel, easy and mild preparation of sulfilimines from sulfoxides using the Burgess reagent", Tetrahedron Letters, Elsevier, Amsterdam, NL, vol. 49, No. 27, Jun. 30, 2008, pp. 4256-4259,XP022695656.

Kita, Noriyasu et al: "Imidazole derivative and silver halide photographic material spectrally sensitized with the compound", 1997, XP002687483. (Abstract Only).

Anton P. et al: "Synthesis of polymeric surfactants by radical thiol/en addition reaction", European Polymer Journal, Pergamon Press Ltd. Oxford, GB, vol. 31, No. 4, Apr. 1, 1995, pp. 387-394.

Koberle and A Laschewsky P: "Hydrophobically Modified Zwitterionic Polymers :Synthesis, Bulk Properties, and Miscibility with Inorganic Salts".Macromolecules, American Chemical Society,Washington, DC; US,vol. 27, Jan. 1, 1994, pp. 2165-2173.

Kupetis, G. et al: "Unsaturated compounds of a pyridine series. (2. Synthesis of sulfobetaines of unsaturated esters of nicotinic acid)", 1985, XP002687484. (Abstract Only).

Emerson Poley Peqanha et al: "Synthesis and pharmacological evaluation of a new class of bicyclic phospholipids, designed as platelet activating factor antagonists", IL Farmaco, vol. 53, No. 5, May 1, 1998, pp. 327-336.

Bayer A.G.: "XRN 4028356", XP002687591,accession No. XRN 4028356 Database accession No. XRN 4028356 ; & DE 12 11 156 B (Bayer AG) Feb. 24, 1966.

Sato, Toshihiro et al: "Ammonium phosphate-containing polymers, lenses using them, and their manufacture", 2000, XP002687477. (Abstract Only).

Nakayama, Takafumi et al: "Presensitized lithographic plates and ethylenic polymers with betaine structures for them", XP002687485, retrieved from STN Database accession No. 2012:338275, abstract.

Bowen, Martina E. et al: "Aqueous fire-fighting foams with reduced fluorine content",(Apr. 5, 2012) XP002687486. (Abstract Only).

Lewis, Andrew L. "Phosphorylcholine-based polymers and their use in the prevention of biofouling." *Colloids and Surfaces B: Biointerfaces* 18.3 (2000): 261-275.

Guillon, Jean-Pierre, Judith Morris, and Brenda Hall. "Evaluation of the pre-lens tear film forming on three disposable contact lenses." *Lacrimal Gland, Tear Film, and Dry Eye Syndromes 3*. Springer US, 2002. 901-915.

Umeda, Takashi, Tadao Nakaya, and Minoru Imoto. "Polymeric phospholipid analogues, 14. The convenient preparation of a vinyl monomer containing a phospholipid analogue." *Die Makromolekulare Chemie, Rapid Communications* 3.7 (1982): 457-459.

Thuong, NT; Chabrier, P. Nouvelle Methode de Preparation de la Phosphorylcholine, de la Phosphorylhomo-choline et de leura WrivBs. Bull. Chem. SOC. Fr. 1974,667-671.

Machine-generated English-language translation of JP-2000-169526, translation generated Mar. 2014, 16 pages.

Machine-generated English-language translation of WO-2010055914, translation generated Mar. 2014, 25 pages.

International Search Report for PCT US2012 053372.

International Search Report for PCT US2012 053370.

International Search Report for PCT US20120 53373.

* cited by examiner

BIOCOMPATIBLE MATERIAL

CROSS-REFERENCE TO RELATED APPLICATIONS

This application claims the benefit of U.S. Provisional Application No. 61/530,120, filed Sep. 1, 2011, and U.S. Provisional Application No. 61/558,066, filed Nov. 10, 2011, under 35 U.S.C. §119(e), and UK Application No. 1115107.3, filed on Sep. 1, 2011, and UK Application No. 1119365.3, filed on Nov. 10, 2011, under 35 U.S.C. §119(a), the disclosures of each of which are incorporated by reference herein in their entireties.

INTRODUCTION

This invention relates to biocompatible materials, in particular monomers and polymers and articles formed therefrom. The materials of the present invention are useful for either coating surfaces of devices or for forming devices from bulk materials where improved biocompatibility is a requirement, for instance where protein adsorption is a concern. The materials are particularly useful in the manufacture of ophthalmic devices, such as contact lenses.

BACKGROUND ART

Materials used in the manufacture of devices which are to be used in contact with protein-containing or biological fluids are selected on the basis of acceptable chemical, physical and mechanical properties and compatibility with the protein-containing or biological fluid. However, it is often difficult to optimise all of these properties simultaneously and so a compromise must be reached which often results in sub-optimal performance. An example is in the manufacture of contact lenses and intraocular lenses which will, in use, be in contact with biological fluids. In particular, contact lenses will be in contact with tear components. The adsorption of tear components onto contact lenses results in deposit formation which is problematic.

In order to avoid these problems occurring, the focus has been on the provision of biocompatible materials which can either be used to coat or form the bulk of such devices to discourage protein adsorption. Biocompatible materials should be capable of reproducible manufacture, be capable of being coated onto surfaces or processed into a suitable form without being degraded or adversely changed, have the requisite mechanical and permeability properties required for the particular application for which they are to be used, be sterilisable without adverse changes in, for example, permeability and mechanical or surface properties, be not damaged or degraded by the biological environment and not be carcinogenic. It is important that such materials do not provoke an unwanted biological response.

An area where biocompatible materials are particularly important is in the manufacture of ocular devices, in particular ophthalmic lenses, in particular contact lenses. This is a key example of a situation where a balance of different properties is required.

Historically, early contact lenses were formed from polymethylmethacrylate which were rigid and allowed very little oxygen through to the cornea. Later, lenses incorporating silicones were made which had improved gas permeability The hydrophobic nature of silicone materials meant that the lenses were easily fouled with tear film components and in certain cases had a tendency to stick to the eye. Furthermore, while lenses formed from such silicones have a high oxygen permeability, the low water content of such materials means that they can be uncomfortable for the wearer. Hence, the focus then shifted to hydrogel systems for the development of more comfortable lenses. Examples of hydrogel systems are those comprising hydroxyethyl methacrylate (HEMA), vinyl pyrrolidone and methacrylic acid or combinations thereof. Such hydrogel systems have a much higher water content than the original rigid gas permeable silicone lenses, and are more conformable and generally less prone to fouling and on-eye dehydration and so are more comfortable for the wearer. However, the oxygen permeability of these materials is not as high as it is for silicones which can increase the risk of corneal damage. In this regard, the oxygen permeability of these lenses may be regarded as adequate for daily use but less suitable for extended wear.

Therefore, more recent research, has been focused on balancing the oxygen permeability associated with silicone materials, with the water content and hydrophilicity (and hence comfort) associated with hydrogel systems. This has led to the development of a class of materials known as silicone hydrogels in which hydrophobic silicone monomers are combined with hydrophilic materials without resulting phase separation which can cause the derived polymer to become translucent or opaque. However, as the contact lenses will be in contact with the surface of the eye, it is also of utmost importance that the silicone hydrogels used to form contact lenses do not elicit any unwanted biological response. As silicone materials are inherently hydrophobic this is a particular challenge because hydrophobicity can cause break up of the tear film on the eye and to surface fouling, both of which can lead to discomfort. Hence, there is a need for biocompatible materials which balance biocompatibility with both high gas, in particular oxygen, permeability and provide a suitably wettable surface As described above, polymerisable vinyl components, such as 2-hydroxyethylmethacrylate and N-vinyl pyrrolidone, have been used to manufacture ophthalmic lenses, and much effort has been devoted to copolymerise such vinyl systems with co-monomers to produce lens materials with improved properties. In particular, 2-(methacryloyloxy-ethyl)-2'(trimethylammonium ethyl)phosphate, inner salt (MPC, hydroxyethyl methacrylate-phosphorylcholine, HEMA-PC), has been used to form biocompatible polymers. These materials contain a zwitterionic phosphorylcholine (PC) group and the biocompatibility of these materials is derived from the fact that this PC group mimics the zwitterionic structure of phospholipids such as phosphatidylcholine and sphingomyelin which are the major components of the outer membrane of all living cells. Contact lens materials incorporating MPC have been shown to possess beneficial properties, including reduced dehydration on eye and reduced deposition of tear film components. More generally, polymers containing zwitterionic groups have been shown to improve biocompatability by reducing protein deposition, blood activation, inflammatory reactions, bacterial adhesion and inhibiting biofilm formation.

A disadvantage of MPC is that is it a solid which has very limited solubility. This places limitations on the utility of MPC as a component in lens formulations.

Furthermore, while MPC has been shown to react with other methacrylate compounds to form co- and ter-polymer systems, the reactions with the other vinyl systems have not been straightforward. This is a consequence of the mismatch in the relative reactivity rates of methacrylate groups and vinyl groups, in addition to the insolubility of MPC in other comonomers In this regard, it has been found that where a mixture of vinyl and methacrylate monomers is polymerised, it will predominantly result in mixtures of polymer derivatives comprising either methacrylate components or vinyl components.

There is a need for new biocompatible materials. In particular, there is a need for materials which impart biocompatibility suitable for the synthesis of biocompatible polymers, particularly biocompatible polymers further comprising residues derived from vinyl co-monomers. Additionally, there is a need for biocompatible monomers which have an improved solubility in, and/or reaction rates comparable with, vinyl monomers, suitable for the synthesis of biocompatible copolymers, particularly biocompatible copolymers useful in the manufacture of devices which are in contact with protein-containing solutions and biological fluids, such as ocular devices, such as contact lenses.

In the field of ocular devices and contact lenses specifically, there is also a need for biocompatible materials which, when formed into such devices, exhibit both a high gas permeability and a wettable surface.

Monomers

The present invention provides ethylenically unsaturated monomers which include both a terminal vinyl group and a zwitterionic group.

Various embodiments of the invention are described herein. It will be recognised that features specified in each embodiment may be combined with other specified features to provide further embodiments.

In this regard, in a first aspect, the present invention provides a monomer of formula (I):

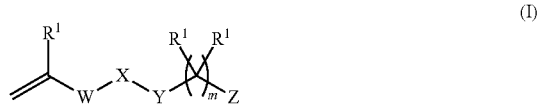

wherein:
W is $(CR^1_2)_n$;
X is O, S or $NR^2$;
Y is a linker group;
Z is a zwitterionic group;
each $R^1$ is independently selected from H, halogen, $C_{1-4}$ alkyl or $C_{1-4}$ haloalkyl;
$R^2$ is H or $C_{1-4}$ alkyl;
n is an integer from 0 to 6; and
m is an integer from 0 to 6.

Advantageously, the monomers of the present invention include both a zwitterionic functionality, to provide improved biocompatibility, and a vinyl group. The presence and nature of the vinyl group means that, where the monomers are to be used in a copolymerisation, a range of comonomers become suitable co-reactants, with better matched reactivity, in particular vinyl comonomers, such as N-vinyl pyrrolidone and N-vinylcarbamates which are already known to be useful in the manufacture of ocular devices, such as contact lenses. The monomers of the present invention, having increased solubility in co-monomer systems can be copolymerized with such co-monomer systems which include siloxane co-monomers to form polymers which are particularly useful for forming ocular devices, in particular ophthalmic lenses, in particular contact lenses. This is a particular advantage as compared to the commonly used material, MPC, which is known to be of very limited solubility.

The value of n may be 0, 1, 2, 3, 4, 5 or 6. In a preferred embodiment, n is 0. In an alternative embodiment, n is 1. In a further embodiment, n is 2. Where n is 0, the vinyl group is adjacent to the heteroatom which means that the lone pair of electrons on the heteroatom can interact with the electrons in the vinyl group which has the effect of increasing the reactivity of the monomer.

In one embodiment, $R^1$ is hydrogen. In an alternative embodiment, $R^1$ is $C_{1-4}$ alkyl, in particular ethyl or methyl, in particular methyl. In an alternative embodiment, $R^1$ may be halogen, in particular fluorine. In an alternative embodiment, $R^1$ may be a $C_{1-4}$ haloalkyl group, wherein one or more of the hydrogen atoms in the alkyl group is substituted with a halogen, in particular fluorine. An example of a $C_{1-4}$ haloalkyl group is $CF_3$. Each $R^1$ group may be the same or different. In one embodiment, the $R^1$ groups are different. In one embodiment, the $R^1$ groups are the same. For example, when n is 1, each of the two $R^1$ groups bound to the carbon atom may be the same or different. Similarly, when n is 2, each of the four $R^1$ groups may be the same or different. Similarly, when n is 1 and m is 1, each of the four $R^1$ groups may be the same or different.

In one embodiment, X is O. In alternative embodiment, X is S. In a further embodiment, X is $NR^2$. In one embodiment, $R^2$ is hydrogen. In one embodiment, $R^2$ is $C_{1-4}$ alkyl, in particular ethyl or methyl, in particular methyl.

Y is a linker group which forms a link between the heteroatom X and the $(CR^1_2)_m Z$ group in the monomer of formula (I). The nature of group Y is not particularly limited and in a preferred embodiment, Y is selected from the group consisting of $C_{1-10}$ alkylene, $C_{2-10}$ alkenylene, $C_{2-10}$ alkynylene, $C_{3-10}$ cycloalkylene, $C_{3-10}$ cycloalkenylene, $C_{1-10}$ heteroalkylene, $C_{2-10}$ heteroalkenylene, $C_{2-10}$ heteroalkynylene, arylene, heteroarylene, —C(O)—, —C(S)—, —C(O)O—, —C(O)S—, —C(O)N($R^M$)—, —C(S)—, —C(S)O—, —C(S)S— and —C(S)N($R^M$)—, wherein $R^M$ is hydrogen or $C_{1-4}$ alkyl. The alkylene, alkenylene, alkynylene, cycloalkylene, cycloalkenylene, heteroalkylene, heteroalkenylene, heteroalkynylene, arylene and heteroarylene groups may be optionally substituted with one or more $R^N$, wherein each $R^N$ is independently selected from the group consisting of —H, —OH, —CN, —NO$_2$, —CF$_3$, —OCF$_3$, —CO$_2$H, —NH$_2$, $C_1$-$C_{10}$ alkyl, $C_2$-$C_{10}$ alkenyl, $C_2$-$C_{10}$ alkynyl, —O($C_1$-$C_{10}$ alkyl), —O($C_2$-$C_{10}$ alkenyl), —O($C_2$-$C_{10}$ alkynyl), halogen, —C(O)H, —C(O)—($C_1$-$C_{10}$ alkyl), —C(O)—O($C_1$-$C_{10}$ alkyl), —NH($C_1$-$C_{10}$ alkyl), —N($C_1$-$C_{10}$ alkyl)$_2$, —C(O)—NH($C_1$-$C_{10}$ alkyl), —C(O)—N($C_1$-$C_{10}$ alkyl)$_2$, —NH—C(O)—($C_1$-$C_{10}$ alkyl), —NH($C_1$-$C_{10}$ alkyl)-C(O)—($C_1$-$C_{10}$ alkyl), —NH—S(O)$_2$—($C_1$-$C_{10}$ alkyl), —NH—($C_1$-$C_{10}$ alkyl)-S(O)$_2$—($C_1$-$C_{10}$ alkyl), —($C_1$-$C_{10}$)—SH, —S(O)—($C_1$-$C_{10}$ alkyl), —S(O)$_2$—($C_1$-$C_{10}$ alkyl), —S(O)$_2$—NH$_2$, —S(O)$_2$—NH—($C_1$-$C_{10}$ alkyl), —S(O)$_2$—N($C_1$-$C_{10}$ alkyl)$_2$ and =O.

In one embodiment, Y is a $C_{1-10}$ alkylene, $C_{2-10}$ alkenylene or $C_{2-10}$ alkynylene optionally substituted with one or more $R^N$. In a further embodiment, Y is $C_{1-6}$ alkylene, $C_{2-6}$ alkenylene or $C_{2-6}$ alkynylene optionally substituted with one or more $R^N$. In a further embodiment, Y is $C_{1-10}$ alkylene, in one instance $C_{1-6}$ alkylene optionally substituted with one or more $R^N$.

In an alternative embodiment, Y is —C(=V)A-, wherein V is S or O and A is selected from $NR^M$, O or S, wherein $R^M$ is H or $C_{1-4}$ alkyl. In particular, in one embodiment, the present invention provides a monomer of formula (IB):

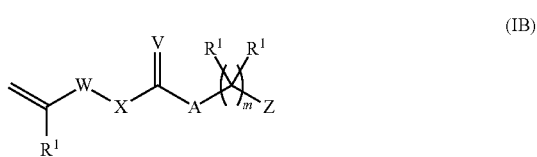

wherein W, X and Z, $R^1$, $R^2$, n and m are as defined above in connection with formula (I), V is S or O; and A is selected from $NR^M$, O and S. Where the monomer of the present invention has formula (IB), preferably V is O and A is O such that Y as defined in formula (I) is —C(O)O—.

In the compounds of formula (I) wherein X is selected from $NR^2$, then $R^2$, Y and the N atom to which they are bonded taken together may form a 5 to 7 membered heterocyclic ring optionally substituted with one or more $R^N$, particularly wherein $R^N$ is O. In particular, $R^2$, Y and the N atom to which they are bonded taken together form a 5-membered heterocyclic ring be optionally substituted with one or more $R^N$, particularly wherein $R^N$ is O.

In one embodiment, the monomer has the formula (IA):

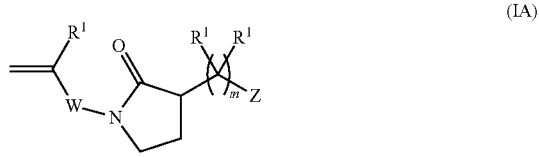

(IA)

wherein W, $R^1$ and Z are as defined above. In one embodiment, the monomer has the formula (IA), wherein n is 0 and hence the group W is not present. In one embodiment, the monomer had the formula (IA), wherein all $R^1$ are H and m is 2.

In alternative embodiment, the monomer has the formula (IAA)

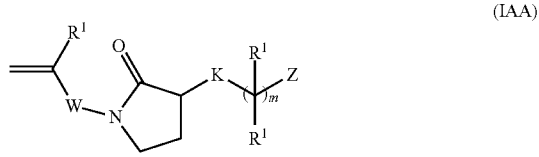

(IAA)

wherein W, $R^1$, m and Z are as defined above and K is selected from the group consisting of $C_{1-10}$ alkylene, $C_{2-10}$ alkenylene, $C_{2-10}$ alkynylene, $C_{3-10}$ cycloalkylene, $C_{3-10}$ cycloalkenylene, $C_{1-10}$ heteroalkylene, $C_{2-10}$ heteroalkenylene, $C_{2-10}$ heteroalkynylene, arylene, heteroarylene, —C(O)—, —C(S)—, —C(O)O—, —C(O)S—, —C(O)N($R^M$)—, —C(S)—, —C(S)O—, —C(S)S— and —C(S)N($R^M$)—, wherein $R^M$ is hydrogen or $C_{1-4}$ alkyl. The alkylene, alkenylene, alkynylene, cycloalkylene, cycloalkenylene, heteroalkylene, heteroalkenylene, heteroalkynylene, arylene and heteroarylene groups may be optionally substituted with one or more $R^N$, wherein each $R^N$ is independently selected from the group consisting of —H, —OH, —CN, —$NO_2$, —$CF_3$, —$OCF_3$, —$CO_2H$, —$NH_2$, $C_1$-$C_{10}$ alkyl, $C_2$-$C_{10}$ alkenyl, $C_2$-$C_{10}$ alkynyl, —O($C_1$-$C_{10}$ alkyl), —O($C_2$-$C_{10}$ alkenyl), —O($C_2$-$C_{10}$ alkynyl), halogen, —C(O)H, —C(O)—($C_1$-$C_{10}$ alkyl), —C(O)—O($C_1$-$C_{10}$ alkyl), —NH($C_1$-$C_{10}$ alkyl), —N($C_1$-$C_{10}$ alkyl)$_2$, —C(O)—NH($C_1$-$C_{10}$ alkyl), —C(O)—N($C_1$-$C_{10}$ alkyl)$_2$, —NH—C(O)—($C_1$-$C_{10}$ alkyl), —NH($C_1$-$C_{10}$ alkyl)-C(O)—($C_1$-$C_{10}$ alkyl), —NH—S(O)$_2$—($C_1$-$C_{10}$ alkyl), —NH—($C_1$-$C_{10}$ alkyl)-S(O)$_2$—($C_1$-$C_{10}$ alkyl), —($C_0$-$C_{10}$)—SH, —S(O)—($C_1$-$C_{10}$ alkyl), —S(O)$_2$—($C_1$-$C_{10}$ alkyl), —S(O)$_2$—$NH_2$, —S(O)$_2$—NH—($C_1$-$C_{10}$ alkyl), —S(O)$_2$—N($C_1$-$C_{10}$ alkyl)$_2$ and =O.

In the compounds of formula (I), the value of m may be 0, 1, 2, 3, 4, 5 or 6. In one embodiment, m is 0. In particular, preferably m is 0 when Y is a group as defined above other than —C(O)—, —C(S)—, —C(O)O—, —C(O)S—, —C(O)N($R^M$)—, —C(S)— or —C(S)N($R^M$)—. In an alternative embodiment, in particular where Y is —C(O)—, —C(S)—, —C(O)O—, —C(O)S—, —C(O)N($R^M$)—, —C(S)— or —C(S)N($R^M$)—, m is 1 or 2.

Z is a zwitterionic group. A zwitterionic group is one which carries both a positive charge and a negative charge located on different atoms within the group such that the net charge of the group is zero. As a consequence, zwitterionic groups have a high polarity and a natural affinity for water. Phospholipids, such as phosphatidylcholine and sphingomyelin, which are the major components of the outer membrane of all living cells have a zwitterionic structure. Hence, because the monomers of the present invention include a zwitterionic group, they can be used to produce polymers which mimic the zwitterionic structure of phospholipids. This improves the biocompatibility of the polymers which the monomers of the present invention may be used to produce.

In one embodiment, Z is a zwitterionic group selected from the group consisting of formula (IIA), (IIB), (IIC), (IID) and (IIE).

In one embodiment, Z is a zwitterionic group of formula (IIB).

Group (IIA) has the formula:

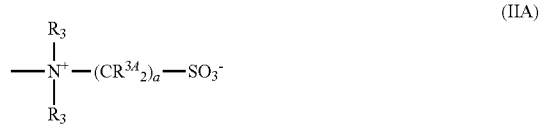

(IIA)

wherein each $R^3$ and $R^{3A}$ is independently selected from hydrogen and $C_{1-4}$ alkyl and a is an integer from 2 to 4.

In one embodiment, both $R^3$ groups are the same. In particular, both $R^3$ groups may be $C_{1-4}$ alkyl, in one embodiment, methyl.

In one embodiment, both $R^{3A}$ groups are the same. In particular, both $R^{3A}$ groups may be hydrogen.

In one embodiment, a is 2 or 3. In a further embodiment, a is 3.

In one embodiment of a monomer of formula (I), where Z is a group of formula (IIA), m is 1 or 2.

Group (IIB) has the formula:

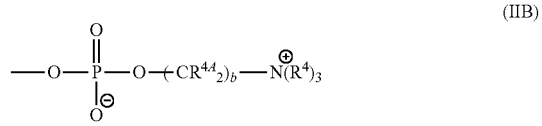

(IIB)

wherein each $R^4$ and $R^{4A}$ is independently selected from hydrogen and $C_{1-4}$ alkyl and b is an integer from 1 to 4;

In one embodiment, all $R^4$ groups are the same. In particular, all $R^4$ groups may be $C_{1-4}$ alkyl, in one embodiment, methyl. In one embodiment, at least one $R^4$ group is $C_{1-4}$ alkyl.

In one embodiment, the $R^{4A}$ groups are the same. In particular, the $R^{4A}$ groups may be hydrogen.

In one embodiment, b is 2 or 3. In a further embodiment, b is 3. Preferably b is 2.

In one embodiment of a monomer of formula (I), where Z is a group of formula (IIB), m is 1 or 2.

In one embodiment, Z is a group of formula (IIB), wherein all $R^4$ groups are methyl groups and b is 2. In this embodiment, Z is a phosphorylcholine (PC) group. PC groups occur naturally in the phospholipids which form the membranes of all living cells. Therefore, with a view to mimicking the zwitterionic properties of phospholipids, it is particularly advantageous for Z to be a PC group.

Group (IIC) has the formula:

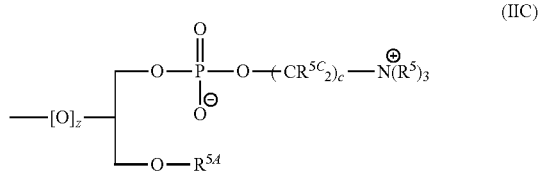

wherein each $R^5$ and $R^{5C}$ is independently selected from hydrogen and $C_{1-4}$ alkyl; $R^{5A}$ is hydrogen or a group —C(O)$B^1R^{5B}$, wherein $R^{5B}$ is hydrogen or methyl, $B^1$ is selected from the group consisting of a bond; $C_{1-4}$ alkylene, $C_{2-10}$ alkenylene, $C_{2-10}$ alkynylene, $C_{3-10}$ cycloalkylene, $C_{3-10}$ cycloalkenylene, $C_{1-10}$ heteroalkylene, $C_{2-10}$ heteroalkenylene, heteroalkynylene, arylene, heteroarylene, wherein the alkylene, alkenylene, alkynylene, cycloalkylene, cycloalkenylene, heteroalkylene, heteroalkenylene, heteroalkynylene, arylene and heteroarylene groups may be optionally substituted with one or more $R^N$ as defined previously, and c is an integer from 1 to 4, wherein if Z is directly bonded to an O or N atom, z is 0 and otherwise z is 1.

In one embodiment, the $R^5$ groups are the same. In particular, the $R^5$ groups may be $C_{1-4}$ alkyl, in one embodiment, methyl. In one embodiment, at least one $R^5$ group is $C_{1-4}$ alkyl.

In one embodiment, both $R^{5C}$ groups are the same. In particular, the $R^{5C}$ groups may be hydrogen.

In one embodiment, c is 2 or 3. In a further embodiment, c is 3.

Group (IID) has the formula:

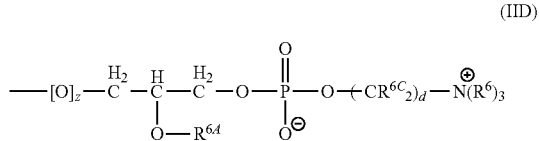

wherein each $R^6$ and $R^{6C}$ is independently selected from hydrogen and $C_{1-4}$ alkyl; $R^{6A}$ is hydrogen or a group —C(O)$B^2R^{6B}$, wherein $R^{6B}$ is hydrogen or methyl, $B^2$ is selected from the group consisting of a bond; $C_{1-10}$ alkylene, $C_{2-10}$ alkenylene, $C_{2-10}$ alkynylene, $C_{3-10}$ cycloalkylene, $C_{3-10}$ cycloalkenylene, $C_{1-10}$ heteroalkylene, $C_{2-10}$ heteroalkenylene, $C_{2-10}$ heteroalkynylene, arylene, heteroarylene, wherein the alkylene, alkenylene, alkynylene, cycloalkylene, cycloalkenylene, heteroalkylene, heteroalkenylene, heteroalkynylene, arylene and heteroarylene groups may be optionally substituted with one or more $R^N$ as defined previously, and d is an integer from 1 to 4, wherein if Z is directly bonded to an O or N atom, z is 0 and otherwise z is 1;

In one embodiment, the $R^6$ groups are the same. In particular, the $R^6$ groups may be $C_{1-4}$ alkyl, in one embodiment, methyl. In one embodiment, at least one $R^6$ group is $C_{1-4}$ alkyl.

In one embodiment, both $R^{6C}$ groups are the same. In particular, the $R^{6C}$ groups may be hydrogen.

In one embodiment, d is 1 or 2. In a further embodiment, d is 2.

Group (IIE) has the formula:

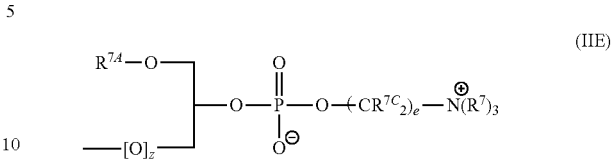

wherein each $R^7$ and $R^{7C}$ is independently selected from hydrogen and $C_{1-4}$ alkyl; $R^{7A}$ is hydrogen or a group —C(O)$B^2R^{7B}$, wherein $R^{7B}$ is hydrogen or methyl, $B^2$ is selected from the group consisting of a bond; $C_{1-10}$ alkylene, $C_{2-10}$ alkenylene, $C_{2-10}$ alkynylene, $C_{3-10}$ cycloalkylene, $C_{3-10}$ cycloalkenylene, heteroalkylene, $C_{2-10}$ heteroalkenylene, $C_{2-10}$ heteroalkynylene, arylene, heteroarylene, wherein the alkylene, alkenylene, alkynylene, cycloalkylene, cycloalkenylene, heteroalkylene, heteroalkenylene, heteroalkynylene, arylene and heteroarylene groups may be optionally substituted with one or more $R^N$ as defined previously, and e is an integer from 1 to 4, wherein if Z is directly bonded to an O or N atom, z is 0 and otherwise z is 1;

In one embodiment, the $R^7$ groups are the same. In particular, the $R^7$ groups may be $C_{1-4}$ alkyl, in one embodiment, methyl. In one embodiment, at least one $R^7$ group is $C_{1-4}$ alkyl.

In one embodiment, both $R^{7C}$ groups are the same. In particular, the $R^{7C}$ groups may be hydrogen.

In one embodiment, e is 1 or 2. In a further embodiment, e is 2.

Further zwitterionic groups are those of formula (IIF), (IIG) and (IIH). These groups contain an alkyl or fluoroalkyl group capable of binding to a surface by physisorption.

Group (IIF) has the formula:

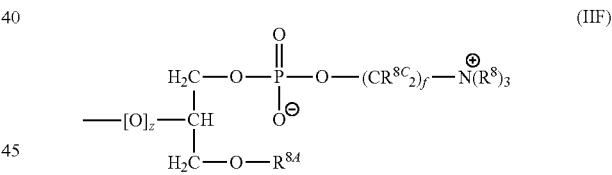

wherein each $R^8$ and $R^{8C}$ is independently selected from hydrogen and $C_{1-4}$ alkyl; $R^{8A}$ is a group —C(O)$B^3R^{8B}$, wherein $R^{8B}$ is hydrogen or methyl, $B^3$ is selected from the group consisting of a bond; $C_{1-10}$ alkylene, $C_{2-10}$ alkenylene, $C_{2-10}$ alkynylene, $C_{3-10}$ cycloalkylene, $C_{3-10}$ cycloalkenylene, $C_{1-10}$ heteroalkylene, $C_{2-10}$ heteroalkenylene, $C_{2-10}$ heteroalkynylene, arylene, heteroarylene, wherein the alkylene, alkenylene, alkynylene, cycloalkylene, cycloalkenylene, heteroalkylene, heteroalkenylene, heteroalkynylene, arylene and heteroarylene groups may be optionally substituted with one or more $R^N$ as defined previously;

f is an integer from 1 to 4, wherein if Z is directly bonded to an O or N atom, z is 0 and otherwise z is 1;

In one embodiment, the $R^{8A}$ groups are the same. In particular, the $R^{8A}$ groups may be $C_{1-4}$ alkyl, in one embodiment, methyl. In one embodiment, at least one $R^{8A}$ group is $C_{1-4}$ alkyl.

In one embodiment, both $R^8$ groups are the same. In particular, the $R^8$ groups may be hydrogen.

In one embodiment, each $R^{8B}$ group is hydrogen.

In one embodiment, $R^{8A}$ is a group —C(O)$B^3R^{8B}$, wherein $B^3$ is a group of formula —[(CR$^{8D}_2)_{aa}$O]$_{bb}$— where the groups —(CR$^{8D}_2$)— are the same or different and in each group —(CR$^{8D}_2$)—, the groups $R^{8D}$ are the same or different and each group $R^{8D}$ is hydrogen, fluorine or $C_{1-4}$ alkyl or fluoroalkyl and aa is from 2 to 6, preferably 3 or 4 and bb is from 1 to 12, preferably 1 to 6. In an embodiment wherein all groups $R^{8D}$ are hydrogen and in all the groups —[(CR$^{8D}_2)_{aa}$O]—, aa is 2, the residues of the monomer of formula (IIF) are not able to form strong secondary valence interactions with hydrophobic surfaces. While residues of such monomers may be included in the polymers of the invention, it is usually also necessary to include residues of monomers which are capable of forming strong secondary valence interactions if such interactions are to bind a polymer to a surface. Monomers which have groups wherein dd is higher than 2 can be used to provide strong secondary valence interactions. In this regard, where $B^3$ is a group of formula —[(CR$^{8D}_2)_{aa}$O]$_{bb}$—, it is advantageous that aa is 2 in about 50 or less, about 70 or less, about 90 mol % or less of the residues —[(CR$^{8D}_2)_{aa}$O]$_{bb}$—.

Group (IIG) has the formula:

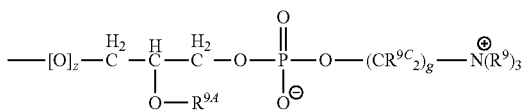

(IIG)

wherein each $R^9$ and $R^{9C}$ is independently selected from hydrogen and $C_{1-4}$ alkyl; $R^{9A}$ is a group —C(O)$B^4R^{9B}$, wherein $R^{9B}$ is hydrogen or methyl, $B^4$ is selected from the group consisting of a bond; $C_{1-10}$ alkylene, $C_{2-10}$ alkenylene, $C_{2-10}$ alkynylene, $C_{3-10}$ cycloalkylene, $C_{3-40}$ cycloalkenylene, $C_{1-10}$ heteroalkylene, $C_{2-10}$ heteroalkenylene, $C_{2-10}$ heteroalkynylene, arylene, heteroarylene, wherein the alkylene, alkenylene, alkynylene, cycloalkylene, cycloalkenylene, heteroalkylene, heteroalkenylene, heteroalkynylene, arylene and heteroarylene groups may be optionally substituted with one or more $R^N$ as defined previously;
g is an integer from 1 to 4, wherein if Z is directly bonded to an O or N atom, z is 0 and otherwise z is 1;

In one embodiment, the $R^{9A}$ groups are the same. In particular, the $R^{9A}$ groups may be $C_{1-4}$ alkyl, in one embodiment, methyl. In one embodiment, at least one $R^{9A}$ group is $C_{1-4}$ alkyl.

In one embodiment, both $R^9$ groups are the same. In particular, the $R^9$ groups may be hydrogen.

In one embodiment, each $R^{9B}$ group is hydrogen.

In one embodiment, $R^{9A}$ is a group —C(O)$B^4R^{9B}$, wherein $B^4$ is a group of formula —[(CR$^{9D}_2)_{cc}$O]$_{dd}$— where the groups —(CR$^{9D}_2$)— are the same or different and in each group —(CR$^{9D}_2$)—, the groups $R^{9D}$ are the same or different and each group $R^{9D}$ is hydrogen, fluorine or $C_{1-4}$ alkyl or fluoroalkyl and cc is from 2 to 6, preferably 3 or 4 and dd is from 1 to 12, preferably 1 to 6. In an embodiment wherein all groups $R^{9D}$ are hydrogen and in all the groups —[(CR$^{9D}_2)_{cc}$O]—, cc is 2, the residues of the monomer of formula (IIG) are not able to form strong secondary valence interactions with hydrophobic surfaces. While residues of such monomers may be included in the polymers of the invention, it is usually also necessary to include residues of monomers which are capable of forming strong secondary valence interactions if such interactions are to bind a polymer to a surface. Monomers which have groups wherein cc is higher than 2 can be used to provide strong secondary valence interactions. In this regard, where $B^4$ is a group of formula —[(CR$^{9D}_2)_{cc}$O]$_{dd}$—, it is advantageous that cc is 2 in about 50 or less, about 70 or less, about 90 mol % or less of the residues —[(CR$^{9D}_2)_{cc}$O]$_{dd}$—.

Group (IIH) has the formula:

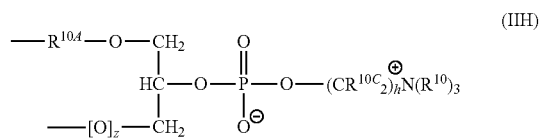

(IIH)

wherein each $R^{10}$ and $R^{10C}$ is independently selected from hydrogen and $C_{1-4}$ alkyl; $R^{10A}$ is a group —C(O)$B^5R^{10B}$, wherein $R^{10B}$ is hydrogen or methyl, $B^5$ is selected from the group consisting of a bond; $C_{1-10}$ alkylene, $C_{2-10}$ alkenylene, $C_{2-10}$ alkynylene, $C_{3-10}$ cycloalkylene, $C_{3-10}$ cycloalkenylene, $C_{1-10}$ heteroalkylene, $C_{2-10}$ heteroalkenylene, $C_{2-10}$ heteroalkynylene, arylene, heteroarylene, wherein the alkylene, alkenylene, alkynylene, cycloalkylene, cycloalkenylene, heteroalkylene, heteroalkenylene, heteroalkynylene, arylene and heteroarylene groups may be optionally substituted with one or more $R^N$ as defined previously;
h is an integer from 1 to 4, wherein if Z is directly bonded to an O or N atom, z is 0 and otherwise z is 1;

In one embodiment, the $R^{10A}$ groups are the same. In particular, the $R^{10A}$ groups may be $C_{1-4}$ alkyl, in one embodiment, methyl. In one embodiment, at least one $R^{10A}$ group is $C_{1-4}$ alkyl.

In one embodiment, both $R^{10}$ groups are the same. In particular, the $R^{10}$ groups may be hydrogen.

In one embodiment, each $R^{10B}$ group is hydrogen.

In one embodiment, $R^{10A}$ is a group —C(O)$B^5R^{10B}$, wherein $B^5$ is a group of formula —[(CR$^{10D}_2)_{ee}$O]$_{ff}$— where the groups —(CR$^{10D}_2$)— are the same or different and in each group —(CR$^{10D}_2$)—, the groups $R^{10D}$ are the same or different and each group $R^{10D}$ is hydrogen, fluorine or $C_{1-4}$ alkyl or fluoroalkyl and ee is from 2 to 6, preferably 3 or 4 and ff is from 1 to 12, preferably 1 to 6. In an embodiment wherein all groups $R^{10D}$ are hydrogen and in all the groups —[(CR$^{10B}_2)_{ee}$O]—, ee is 2, the residues of the monomer of formula (IIH) are not able to form strong secondary valence interactions with hydrophobic surfaces. While residues of such monomers may be included in the polymers of the invention, it is usually also necessary to include residues of monomers which are capable of forming strong secondary valence interactions if such interactions are to bind a polymer to a surface. Monomers which have groups wherein ee is higher than 2 can be used to provide strong secondary valence interactions. In this regard, where $B^5$ is a group of formula —[(CR$^{10d}_2)_{ee}$O]$_{ff}$—, it is advantageous that ee is 2 in about 50 or less, about 70 or less, about 90 mol % or less of the residues —[(CR$^{10D}_2)_{ee}$O]$_{ff}$—.

Exemplary Monomers of Formula (I)

In one embodiment, the present invention provides a monomer of formula (I), which has the formula (IB):

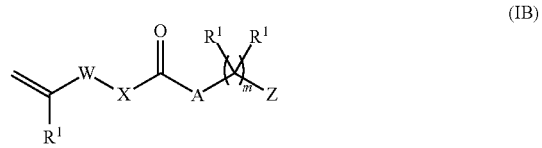

(IB)

wherein W, X, Z, A, $R^1$, $R^2$, n and m are as defined previously in connection with formula (I).

In one embodiment, the present invention provides a monomer of formula (IB), wherein X is O, particularly wherein A is O, particularly wherein A is O and Z is a group of formula IIB, particularly wherein A is O, n is 0 and Z is a group of formula IIB, particularly wherein A is O, n is 0 and Z is a group of formula IIB, wherein each $R^4$ is methyl and b is 2.

In one embodiment, the present invention provides a monomer of formula (IB), wherein X is $NR^2$, particularly wherein A is O, particularly wherein A is O and Z is a group of formula IIB, particularly wherein A is O, n is 0 and Z is a group of formula IIB, particularly wherein A is O, n is 0 and Z is a group of formula IIB, wherein each $R^4$ is methyl and b is 2.

In one embodiment, the present invention provides a monomer of formula (IB), wherein X is O and A is $NR^M$, particularly, wherein Z is a group of formula IIB, particularly wherein Z is a group of formula IIB and n is 0, particularly wherein n is 0 and Z is a group of formula IIB, wherein each $R^4$ is methyl and b is 2.

In one embodiment, the present invention provides a monomer of formula (IB), wherein X is $NR^2$, particularly wherein A is O, particularly wherein A is O and Z is a group of formula IIB, particularly wherein A is O, n is 0 and Z is a group of formula IIB, particularly wherein A is O, n is 0 and Z is a group of formula IIB, wherein each $R^4$ is methyl and b is 2.

In one embodiment, the present invention provides a monomer of formula (IB), wherein X is $NR^2$ and A is $NR^M$, particularly wherein Z is a group of formula IIB, particularly wherein n is 0 and Z is a group of formula IIB, particularly wherein n is 0 and Z is a group of formula IIB, wherein each $R^4$ is methyl and b is 2.

In one embodiment, the present invention provides a monomer of formula (IC):

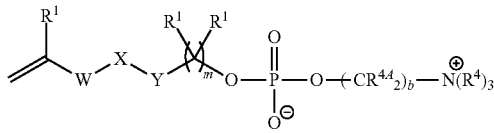

(IC)

wherein W, X, Y, $R^1$, $R^2$, $R^4$, $R^{4A}$, m, n and b are as defined previously.

In one embodiment, the present invention provides a monomer of formula (IC), wherein X is O.

In one embodiment, the present invention provides a monomer of formula (IC), wherein X is $NR^2$.

In one embodiment, the present invention provides a monomer of formula (IC), wherein X is $NR^2$ and n is 0, particularly wherein m is 2, particularly wherein m is 2 and Y, $R^2$ and the N atom to which they are bonded together form a 5 to 7-membered heterocyclic ring, preferably a 5-membered heterocyclic ring.

In one embodiment, the present invention provides a monomer of formula (IC), wherein X is $NR^2$, n is 0, m is 2 and Y, $R^2$ and the N atom to which they are bonded together form a 5-membered heterocyclic ring, each $R^4$ is methyl and b is 2.

In one embodiment, the present invention provides a monomer of formula (ID):

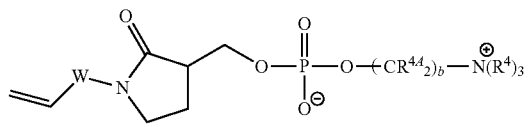

(ID)

wherein W, $R^4$, $R^{4A}$ and b are as defined previously.

In one embodiment, the present invention provides a monomer of formula (IE):

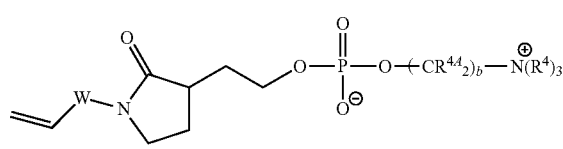

(IE)

wherein W, $R^4$, $R^{4A}$ and b are as defined previously.

Methods of Manufacture

The monomers of the present invention may be prepared by conventional techniques using known reactions.

In general, there are three routes by which the monomers may be synthesized, specifically:
(i) reaction of a nucleophilic zwitterionic derivative with a reactive vinyl derivative;
(ii) reaction of a nucleophilic vinyl compound with a reactive zwitterionic derivative; or
(iii) reaction of a nucleophilic vinyl compound with a phospholane followed by ring opening with a trialkylamine.

Chemical Groups

Halo

The term "halogen" (or "halo") is used herein to refer to fluorine, chlorine, bromine and iodine.

Carbonyl and Carboxy

The term "carbonyl" is used herein to refer to a carbon connected with a double bond to an oxygen atom, and tautomeric forms thereof. A carbonyl group may also be denoted as —C(O)—. Examples of moieties that contain a carbonyl include but are not limited to aldehydes —C(O)H, ketones —C(O)—($C_1$-$C_{10}$ alkyl)-, carboxylic acids —$CO_2H$ and amides —C(O)$NH_2$, —C(O)—NH($C_1$-$C_{10}$ alkyl), —C(O)—N($C_1$-$C_{10}$ alkyl)$_2$, —NH—C(O)—($C_1$-$C_{10}$ alkyl), —NH($C_1$-$C_{10}$ alkyl)-C(O)—($C_1$-$C_{10}$ alkyl) and esters —C(O)—O($C_1$-$C_{10}$ alkyl).

Thiocarbonyl and Thiocarboxy

The terms "thiocarbonyl" and "thiocarboxy" are used herein to refer to a carbon connected via a double bond to a sulfur atom, and tautomeric forms thereof.

Alkyl, Alkenyl, Cycloalkyl etc.

The term "alkyl" is used herein to refer to monovalent straight chain or branched, saturated, acyclic hydrocarbyl groups. In one embodiment, alkyl is $C_{1-10}$alkyl, in another embodiment $C_{1-6}$alkyl, in another embodiment $C_{1-4}$alkyl, such as methyl, ethyl, n-propyl, i-propyl or i-, n-, secondary or t-butyl groups.

The term "cycloalkyl" is used herein to refer to monovalent, saturated, cyclic hydrocarbyl groups. In one embodiment, cycloalkyl is $C_{3-10}$cycloalkyl, in another embodiment, $C_{3-6}$cycloalkyl, such as cyclopentyl and cyclohexyl.

The term "alkenyl" is used herein to refer to monovalent straight or branched, unsaturated, acyclic hydrocarbyl groups having at least one carbon-carbon double bond and, in one embodiment, no carbon-carbon triple bonds. In one embodiment alkenyl is $C_{2-10}$alkenyl, in another embodiment, $C_{2-6}$alkenyl, in another embodiment $C_{2-4}$alkenyl.

The term "cycloalkenyl" is used herein to refer to monovalent, unsaturated, cyclic hydrocarbyl groups. In one embodiment, cycloalkenyl is $C_{3-10}$cycloalkyl, in another embodiment, $C_{3-6}$cycloalkyl, such as cyclopentenyl and cyclohexenyl.

The term "alkynyl" is used herein to refer to monovalent straight or branched, unsaturated, acyclic hydrocarbyl groups having at least one carbon-carbon triple bond. In one embodiment alkynyl is $C_{2-10}$alkynyl, in another embodiment, $C_{2-6}$alkynyl, in another embodiment $C_{2-4}$alkynyl.

Heteroalkyl, Heterocyclyl etc.

The term "heteroalkyl" is used herein to refer to monovalent alkyl groups in which up to three carbon atoms, in one embodiment up to two carbon atoms, in another embodiment one carbon atom, are each replaced independently by O, $S(O)_q$ or N, provided at least one of the alkyl carbon atoms remains. The heteroalkyl group may be C-linked or hetero-linked, i.e. it may be linked to the remainder of the molecule through a carbon atom or through O, $S(O)_q$ or N, wherein q is independently 0, 1 or 2.

The term "heterocyclyl" or "heterocyclic ring" is used herein to refer to monovalent, cycloalkyl groups or divalent cycloalkylene groups in which up to three carbon atoms, in one embodiment up to two carbon atoms, in another embodiment one carbon atom, are each replaced independently by O, $S(O)_q$ or N, provided at least one of the cycloalkyl carbon atoms remains.

Examples of heterocyclyl groups include oxiranyl, thiaranyl, aziridinyl, oxetanyl, thiatanyl, azetidinyl, tetrahydrofuranyl, tetrahydrothiophenyl, pyrrolidinyl, pyrazolidinyl, imidazolidinyl, tetrahydropyranyl, tetrahydrothiopyranyl, piperidinyl, 1,4-dioxanyl, 1,4-oxathianyl, morpholinyl, 1,4-dithianyl, piperazinyl, 1,4-azathianyl, oxepanyl, thiepanyl, azepanyl, 1,4-dioxepanyl, 1,4-oxathiepanyl, 1,4-oxaazepanyl, 1,4-dithiepanyl, 1,4-thieazepanyl and 1,4-diazepanyl. Other examples include cyclic imides, cyclic anhydrides and thiazolidindiones. The heterocyclyl group may be C-linked or N-linked, i.e. it may be linked to the remainder of the molecule through a carbon atom or through a nitrogen atom.

Aryl etc.

The term "aryl" is used herein to refer to monovalent, aromatic, cyclic hydrocarbyl groups, such as phenyl or naphthyl (e.g. 1-naphthyl or 2-naphthyl). In general, the aryl group may be a monocyclic or polycyclic fused ring aromatic group. Preferred aryl groups are $C_6$-$C_{14}$aryl.

Other examples of aryl groups are monovalent radicals derived from aceanthrylene, acenaphthylene, acephenanthrylene, anthracene, azulene, chrysene, coronene, fluoranthene, fluorene, as-indacene, s-indacene, indene, naphthalene, ovalene, perylene, phenalene, phenanthrene, picene, pleiadene, pyrene, pyranthrene and rubicene.

Heteroaryl etc.

The term "heteroaryl" is used herein to refer to monovalent, heteroaromatic, cyclic hydrocarbyl groups additionally containing one or more heteroatoms independently selected from O, S, N and $NR^N$, wherein $R^N$ is preferably H, alkyl (e.g. $C_{1-6}$alkyl) or cycloalkyl (e.g. $C_{3-6}$cycloalkyl).

In general, the heteroaryl group may be a monocyclic or polycyclic (e.g. bicyclic) fused ring heteroaromatic group. In one embodiment, heteroaryl groups contain 5-13 ring members (preferably 5-10 members) and 1, 2, 3 or 4 ring heteroatoms independently selected from O, S, N and $NR^N$. In one embodiment, a heteroaryl group may be 5, 6, 9 or 10 membered, e.g. 5-membered monocyclic, 6-membered monocyclic, 9-membered fused-ring bicyclic or 10-membered fused-ring bicyclic.

Monocyclic heteroaromatic groups include heteroaromatic groups containing 5-6 ring members and 1, 2, 3 or 4 heteroatoms selected from O, S, N or $NR^N$.

In one embodiment, 5-membered monocyclic heteroaryl groups contain 1 ring member which is an —$NR^N$— group, an —O— atom or an —S— atom and, optionally, 1-3 ring members (e.g. 1 or 2 ring members) which are =N— atoms (where the remainder of the 5 ring members are carbon atoms).

Examples of 5-membered monocyclic heteroaryl groups are pyrrolyl, furanyl, thiophenyl, pyrazolyl, imidazolyl, isoxazolyl, oxazolyl, isothiazolyl, thiazolyl, 1,2,3 triazolyl, 1,2,4 triazolyl, 1,2,3 oxadiazolyl, 1,2,4 oxadiazolyl, 1,2,5 oxadiazolyl, 1,3,4 oxadiazolyl, 1,3,4 thiadiazolyl and tetrazolyl.

Examples of 6-membered monocyclic heteroaryl groups are pyridinyl, pyridazinyl, pyrimidinyl, pyrazinyl, 1,3,5 triazinyl, 1,2,4 triazinyl and 1,2,3 triazinyl.

In one embodiment, 6-membered monocyclic heteroaryl groups contain 1 or 2 ring members which are =N— atoms (where the remainder of the 6 ring members are carbon atoms).

Bicyclic heteroaromatic groups include fused-ring heteroaromatic groups containing 9-13 ring members and 1, 2, 3, 4 or more heteroatoms selected from O, S, N or $NR^N$.

In one embodiment, 9-membered bicyclic heteroaryl groups contain 1 ring member which is an —$NR^N$— group, an —O— atom or an —S— atom and, optionally, 1-3 ring members (e.g. 1 or 2 ring members) which are =N— atoms (where the remainder of the 9 ring members are carbon atoms).

Examples of 9-membered fused-ring bicyclic heteroaryl groups are benzofuranyl, benzothiophenyl, indolyl, benzimidazolyl, indazolyl, benzotriazolyl, pyrrolo[2,3-b]pyridinyl, pyrrolo[2,3-c]pyridinyl, pyrrolo[3,2-c]pyridinyl, pyrrolo[3,2-b]pyridinyl, imidazo[4,5-b]pyridinyl, imidazo[4,5-c]pyridinyl, pyrazolo[4,3-d]pyridinyl, pyrazolo[4,3-c]pyridinyl, pyrazolo[3,4-c]pyridinyl, pyrazolo[3,4-b]pyridinyl, isoindolyl, indazolyl, purinyl, indolininyl, imidazo[1,2-a]pyridinyl, imidazo[1,5-a]pyridinyl, pyrazolo[1,2-a]pyridinyl, pyrrolo[1,2-b]pyridazinyl and imidazo[1,2-c]pyrimidinyl.

In one embodiment, 10-membered bicyclic heteroaryl groups contain 1-3 ring members which are =N— atoms (where the remainder of the 10 ring members are carbon atoms).

Examples of 10-membered fused-ring bicyclic heteroaryl groups are quinolinyl, isoquinolinyl, cinnolinyl, quinazolinyl, quinoxalinyl, phthalazinyl, 1,6-naphthyridinyl, 1,7-naphthyridinyl, 1,8-naphthyridinyl, 1,5-naphthyridinyl, 2,6-naphthyridinyl, 2,7-naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b]pyrazinyl and pyrimido[4,5-d]pyrimidinyl.

In some embodiments, a heterocyclyl group may be fused to an aryl or heteroaryl group to form a bicyclic ring system containing 5 to 13 members. Examples of such groups include dihydroisoindolyl, dihydroindolyl, tetrahydroisoquinolinyl, tetrahydroquinolinyl or 2,3-dihydro-pyrrolyl-[2,3-b]pyridine.

Alkoxy

The terms "alkoxy" and "alkyloxy" are used herein to refer to an —O-alkyl group in which alkyl is as described above. Exemplary alkoxy groups include methoxy (—OCH$_3$) and ethoxy (—OC$_2$H$_5$).

Alkylene

The term "alkylene" is used herein to refer to a divalent-alkyl-group in which alkyl is as defined previously. Exemplary alkylene groups include —CH$_2$—, —(CH$_2$)$_2$— and —C(CH$_3$)HCH$_2$—.

Alkenylene

The term "alkenylene" is used herein to refer to a divalent-alkenyl-group in which alkenyl is as defined previously. Exemplary alkenylene groups include —CH=CH—, —CH=CHCH$_2$—, and —CH$_2$CH=CH—.

Alkynylene

The term "alkynylene" is used herein to refer to a divalent-alkynyl-group in which -alkynyl- refers to a straight or branched chain hydrocarbon group having from 2 to 12, conveniently 2 to 6, carbon atoms and one carbon-carbon triple bond in the chain. Exemplary alkynylene groups include ethynyl and propargyl.

Arylene

The term "arylene" is used herein to refer to a divalent-aryl-group where aryl is as described above which is linked to two or more other groups. Examples of arylene groups include phenylene.

"Phenylene" means a -phenyl-group. Exemplary groups are 1,3-phenylene and 1,4-phenylene.

Heteroarylene

The term "heteroarylene" is used herein to refer to a -heteroaryl-group, where heteroaryl is as described above, which is linked to two or more other groups. Exemplary groups include 2,5-furyl, 2,5-thienyl, 2,4-thiazolyl, 2,5-thiazolyl and 2,6-pyridyl.

As used herein, the term "nucleophilic" has its conventional meaning and refers to a derivative which includes a group that forms a bond with another species (an electrophile) by donating an electron pair.

The term "vinyl compound" refers to a compound which includes a terminal —CH=CH$_2$ group.

Examples of nucleophilic groups include alcohols, peroxides, alkoxide anions, carboxylate anions, ammonia, amines, azides, nitrites, thiols, (RSH), thiolate anions (RS$^-$), anions of thiolcarboxylic acids (RC(O)—S$^-$), and anions of dithiocarbonates (RO—C(S)—S$^-$) and dithiocarbamates (R$_2$N—C(S)—S$^-$).

In the general reaction (i) described above, the reactive vinyl derivative will include an electrophilic group which reacts with the nucleophilic zwitterionic or zwitterionic precursor derivative. Hence, the reactive vinyl derivative can be described by the general formula C=C—W—X-E, wherein W and X are as defined for formula (I) and E is an electrophilic group. The skilled person will be familiar with suitable reagents which may be used as the reactive vinyl derivative. Examples of suitable reactive vinyl derivatives include vinylchloroformate and vinyl isocyanate.

In one embodiment, the reactive vinyl derivative is an N-vinyl lactam derivative. N-vinyl lactams have properties which are useful in the preparation of contact lenses. For example, N-vinyl pyrrolidone is a compound which is commonly used in the manufacture of contact lenses. Hence, it would be advantageous to provide a biocompatible co-monomer which is reactive with this compound.

The reactive vinyl derivative is reacted with a nucleophilic derivative of a zwitterion or zwitterionic precursor which may be depicted generally as having a structure A$^1$-(CR$^1$)$_m$—Z, wherein A$^1$ is a nucleophilic group containing a heteroatom selected from N, O and S. For example, A$^1$ may be selected from the group consisting of alcohols, peroxides, alkoxide anions, carboxylate anions, ammonia, amines, azides, nitrites, thiols (RSH), thiolate anions (RS$^-$), anions of thiolcarboxylic acids (RC(O)—S$^-$), and anions of dithiocarbonates (RO—C(S)—S$^-$) and dithiocarbamates (R$_2$N—C(S)—S$^-$).

Examples of suitable nucleophilic derivatives of a zwitterion include but are not limited to hydroxyethylphosphorylcholine and aminoethylphosphorylcholine.

Examples of suitable nucleophilic derivatives of a zwitterionic precursor include but are not limited to ethylene glycol or monoprotected derivatives thereof and aminoethanol.

As described above, in one embodiment the zwitterionic group Z is a group of formula (IIB), in particular a phosphorylcholine group. Synthetic routes for adding a PC group to a monomer are known in the art. For example, Chabrier et al. describes a two step reaction which involves reacting a hydroxyl substituted starting material with a halophospholane and then ring opening with a trialkylamine in FR-A-2270887 and Bul. Soc. Chim de France (1974) 667-671. An analogous two stage reaction for producing HEMA-PC was described by Nakaya et al in JP-A-58-154591 and Makromol. Chem., Rapid Commun., 1982, 3, 457. A more recent synthetic route is described in EP-A-0730 599.

Monomers of formula (IB) may be synthesized using reaction (i) above, wherein the reactive vinyl derivative used has the formula (IIIA):

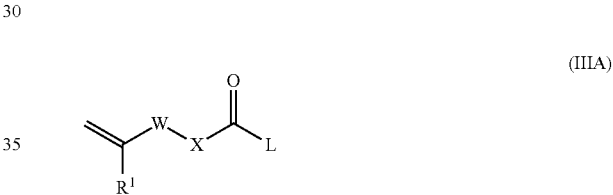

(IIIA)

wherein W, X and R$^1$ are as defined above and L is a leaving group which, together with the carbonyl group, forms an electrophilic group which reacts with the nucleophilic derivative of a zwitterion or zwitterionic precursor. The skilled person will be familiar with suitable leaving groups. Examples of suitable leaving groups include halogens, amine moieties, alkoxy, allylthio, triflates, mesylates, tosylates and fluorosulphonates.

Alternatively, where X in formula (IB) is N, a vinyl isocyanate, i.e. a compound of formula (IIIB) or a vinyl isothiocyanate, i.e. a compound of formula (IIIC), may be used as the reactive vinyl derivative:

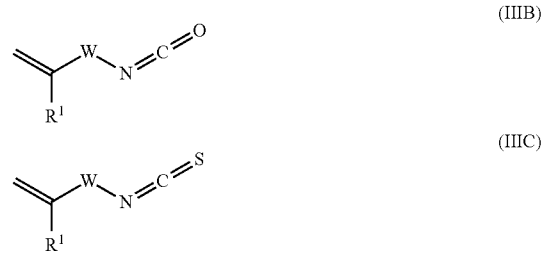

(IIIB)

(IIIC)

With reference to the general reaction (ii) described above, the nucleophilic vinyl compound is one which includes both a nucleophilic group and a vinyl group. It has the general structure C=C—W—X—Y—(CR$^1$)$_m$-Nuc, wherein "Nuc"

is a nucleophilic group. Examples of suitable nucleophilic groups include but are not limited to —OH, —NH$_2$, NHR, SH and suitable anions, including carboxylate anions. In one embodiment, the nucleophilic vinyl compound is an N-vinyl lactam derivative, in particular a derivative of N-vinyl pyrrolidone. N-vinyl lactam derivatives may be formed by reacting an N-vinyl lactam with a base to form an anion at position 3 on the ring (adjacent to the carbonyl group) and then subsequently reacting the anion with, for example, iodooethanol, to form a 3-hydroxyethyl-substituted lactam.

In one embodiment, the nucleophilic vinyl derivative may have the formula:

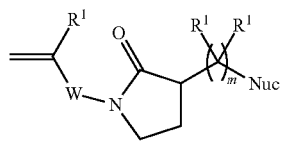

The nucleophilic vinyl compound is reacted with a reactive zwitterionic derivative having the general formula Z-L, wherein L is a leaving group as defined above in connection with reaction scheme (i). Examples of suitable reactive zwitterionic derivatives include but are not limited to those having a leaving group selected from the group consisting of tosyl-, mesyl-, fluorosulphonate-, triflate-, imidazolecarbonyloxy-, halo, amononiumalkyl, epoxyalkyl, alkoxycarbonyl, alkylthiocarbonyl and alkylcarbonyloxycarbonylalkyl.

In one embodiment of the present invention, the zwitterionic group in the monomers of the present invention is a group of formula (IIB), specifically a phosphorylcholine type group.

Monomers of formula (IA), wherein Z is a group of formula (IIB) may alternatively be formed by a reaction (iii), wherein a nucleophilic vinyl compound, such as those described above in connection with reaction scheme (ii), is reacted with a phospholane followed by ring opening with a trialkylamine.

Monomers of formula (IC), wherein b is 2, may be synthesized by reacting a nucleophilic vinyl derivative of formula (V):

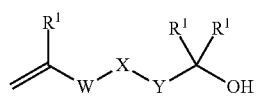

with a phospholane reagent (VIA) or (VIB):

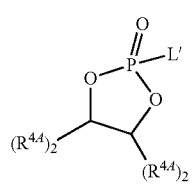

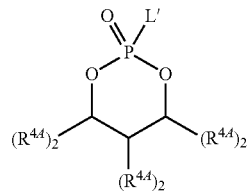

wherein each $R^{44}$ is independently selected from the group consisting of H and $C_{1-4}$ alkyl and L' is a leaving group. The skilled person will be familiar with suitable leaving groups. Examples of suitable leaving groups include halogens, amine moieties, alkoxy, allylthio, triflates, mesylates, tosylates and fluorosulphonates.

Reaction with a phospholane reagent (VIA) forms an intermediate compound of formula (VII):

(VII)

which can then be reacted with a trialkylamine reagent $N(R^4)_3$, wherein each $R^4$ is independently hydrogen or $C_{1-4}$ alkyl to produce a compound of formula (IC).

Phospholane reagents of formula (VIA) and (VIB) are commercially available and methods for synthesizing phospholane reagents are known in the art (N. Thung, M Chassignol, U. Asseline and P. Chalvier, Bull. Soc. Chim. Fr. 1981 (Part 2) 51). The skilled person will also be familiar with the fact that suitable substituted phosphorus compounds may also be used in place of a phospholane reagent. In one embodiment, in the phospholane reagent (VI), each $R^{44}$ is hydrogen. In one embodiment, the phospholane reagent is ethylenechlorophosphate (ECP) (CAS 6609-64-9,2-chloro-1,3,2-dioxaphospholane-2-oxide). It is advantageous to minimise the presence of impurities in the phospholane reagent to avoid side reactions and this can be monitored by $^{31}P$ NMR.

Trialkylamine reagents are commercially available. Examples of suitable trialkylamine reagents include trimethylamine and triethylamine. In one embodiment, the trialkylamine reagent is trimethylamine i.e. each $R^4$ is methyl.

In one embodiment, the first step may be carried out in a first suitable solvent in which the compound of formula (V) and the phospholane reagents (VIA) and (VIB) are soluble, and in which an acid scavenger is insoluble. For the second step, a nitrile in particular, a nitrile derivative of a $C_{1-6}$ carboxylic acid, preferably acetonitrile may be advantageously used or a nitrile solvent may be used for both the first and second steps.

Polymers

The monomers of the present invention are useful in producing biocompatible polymers which can be used in biocompatible coatings and in forming bulk materials and devices. Therefore, in a further aspect, the present invention provides polymers derived from co-polymerizing a monomer of formula (I) as defined herein with one or more co-monomers.

The polymers of the present invention are biocompatible and advantageously can be used to produce articles which have both a high gas, in particular oxygen permeability and a high water content.

The polymers of the present invention may be produced by conventional polymerization reactions, for example by thermal or photochemical polymerization. For thermal polymerisation, a temperature in the range from 40 to 100° C., typically 50 to 80° C. may be used. For a photochemical polymerisation, actinic radiation such as gamma, UV, visible or microwave radiation may be use. Typically UV radiation of wavelength 200 to 400 nm is used.

The polymerisation is generally performed in a reaction medium, which is for instance a solution or dispersion using a solvent with which the groups present in the monomers will not react under the polymerisation conditions used, for example water, alcohols, such as ethanol, methanol and glycol, and furthermore carboxylic acid amides, such as dimethylformamide, dipolar aprotic solvents, such as dimethyl sulfoxide or methyl ethyl ketone, ketones for example acetone or cyclohexanone, hydrocarbons, for example toluene, ethers, for example THF, dimethoxyethane or dioxane and halogenated hydrocarbons, for example trichloroethane and also mixtures of suitable solvents, for example mixtures of water with an alcohol, for example a water/ethanol or water/methanol mix. Any mixtures of these solvents may be used. Alternatively the polymerisation may be carried out in the absence of a solvent or where a co-monomer acts as the solvent.

The polymerisation may be carried out in the presence of one or more polymerisation initiators, such as benzoyl peroxide, 2,2'-azo-bis(2-methylpropionitrile) or benzoin methyl ether. Other polymerisation initiators which may be used are disclosed in "Polymer Handbook", 3rd Edition, Ed. J. Brandrup and E. H. Immergut, Pub. Wiley-Interscience, New York 1989.

Generally, the copolymerisation is performed for 0.1 to 72 hours, in one embodiment, 0.1 to 1 hours, in an alternative embodiment, 8 to 48 hours, for instance 16 to 24 hours and under an inert atmosphere of, for example, nitrogen or argon.

The polymer is generally purified by dialysis, precipitation in a non-solvent (e.g. diethyl ether or acetone) or ultrafiltration. The resulting polymer is generally dried under vacuum e.g. for 5 to 72 hours and has a molecular weight from 10,000 to 10 million, in one instance, from 20,000 to 1 million, in an alternative instance, from 50,000 to 750,000, in an alternative instance, from 50,000 to 500,000.

Where the aim is to provide a biocompatible coating and co-monomers capable of producing cross-linking are present in the monomer mixture, the polymerisation conditions are set such that cross-linking does not occur during polymerisation. For example, actinic radiation would not be used to prepare polymer containing a co-monomer which can form crosslinks by exposure to actinic radiation.

The precise nature of the co-monomer system with which the monomers of the present invention are co-polymerized will depend on the intended use of the polymer which is produced.

Advantageously, where the polymer is intended for use in forming ocular devices such as contact lenses, the monomers of the present invention are reacted with a co-monomer system which includes a siloxane group-containing monomer or macromer.

A siloxane group-containing component is one which includes the residue having the general structure —[Si(R)$_2$O]—, wherein R is hydrogen or a C$_{1-10}$ alkylene, C$_{2-10}$ alkenylene, C$_{2-10}$ alkynylene, C$_{3-10}$ cycloalkylene, C$_{3-10}$ cycloalkenylene, C$_{1-10}$ heteroalkylene, C$_{2-10}$ heteroalkenylene, C$_{2-10}$ heteroalkynylene, arylene, heteroarylene group. Preferably R is a C$_{1-10}$ alkylene group, preferably a C$_1$ alkylene group. Preferably, the Si and attached 0 are present in the siloxane group-containing monomer or macromer in an amount greater than 20 weight percent, and more preferably greater than 30 weight percent of the total molecular weight of the siloxane group-containing monomer or macromer.

Useful siloxane group-containing monomer or macromer may comprise polymerizable functional groups such as acrylate, methacrylate, acrylamide, methacrylamide, N-vinyl lactam, N-vinylamide, and styryl functional groups. Examples of siloxane group-containing components which may be included in the co-solvent system are described in U.S. Pat. No. 3,808,178, U.S. Pat. No. 4,120,570, U.S. Pat. No. 4,136,250, U.S. Pat. No. 4,153,641, U.S. Pat. No. 4,740,533, U.S. Pat. No. 5,034,461, U.S. Pat. No. 5,070,215 and EP 080539. All of the patents cited herein are hereby incorporated in their entireties by reference.

In one embodiment of the present invention, the siloxane group-containing monomer may be a polysiloxanylalkyl (meth)acrylic monomer represented by the following formula X:

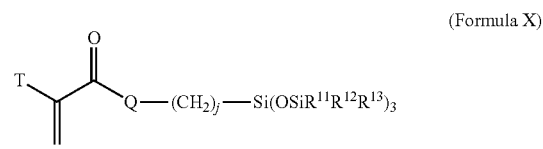

(Formula X)

wherein: T denotes H or lower alkyl and in certain embodiments H or methyl; Q denotes O or NR$^{14}$; each R$^{14}$ independently denotes hydrogen or methyl, each R$^{11}$, R$^{12}$ and R$^{13}$ independently denotes a lower alkyl radical or a phenyl radical, and j is 1 or 3 to 10. Examples of these polysiloxanylalkyl (meth)acrylic monomers include methacryloxypropyl tris(trimethylsiloxy) silane, pentamethyldisiloxanyl methylmethacrylate, and methyldi(trimethylsiloxy)methacryloxymethyl silane.

An alternative class of siloxane group-containing components which may form a part of the co-solvent system are poly(organosiloxane) prepolymers represented by Formula XI:

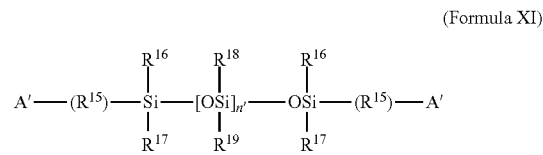

(Formula XI)

wherein: each A' independently denotes an activated unsaturated group, such as an ester or amide of an acrylic or a methacrylic acid or an alkyl or aryl group (providing that at least one A' comprises an activated unsaturated group capable of undergoing radical polymerization); each of R$^{16}$, R$^{17}$, R$^{18}$ and R$^{19}$ are independently selected from the group consisting of a monovalent hydrocarbon radical or a halogen substituted monovalent hydrocarbon radical having 1 to 18 carbon atoms which may have ether linkages between carbon atoms; R$^{15}$ denotes a divalent hydrocarbon radical having from 1 to 22 carbon atoms, and n' is 0 or an integer greater than or equal to 1, in one embodiment n' is 5 to 400, in another embodiment n' is 10 to 300. One specific example is α,ω-bismethacryloxypropyl poly-dimethylsiloxane. Another example is mPDMS (monomethacryloxypropyl terminated mono-n-butyl terminated polydimethylsiloxane).

Another useful class of siloxane group-containing components includes silicone-containing vinyl carbonate or vinyl carbamate monomers of the following formula XII:

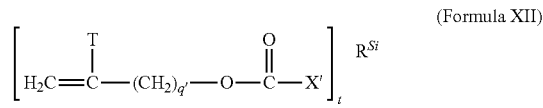

(Formula XII)

wherein: X' denotes O, S or NH; $R^{Si}$ denotes a silicone-containing organic radical; T denotes hydrogen or lower alkyl, in certain embodiments H or methyl; t is 1, 2, 3 or 4; and q' is 0 or 1. Suitable silicone-containing organic radicals $R^{Si}$ include the following:

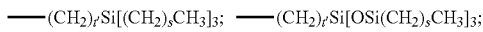

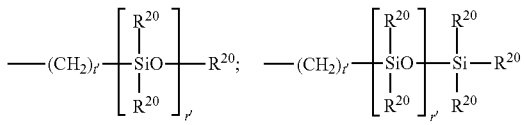

wherein $R^{20}$ denotes

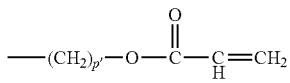

wherein p' is 1 to 6; or an alkyl radical or a fluoro-alkyl radical having 1 to 6 carbon atoms; r' is 1 to 200, t' is 1, 2, 3 or 4; and s is 0, 1, 2, 3, 4 or 5.

The siloxane group-containing vinyl carbonate or vinyl carbamate monomers specifically include: 1,3-bis[4-(vinyloxycarbonyloxy)but-1-yl]tetramethyl-isiloxane 3-(vinyloxycarbonylthio) propyl-[tris(trimethylsiloxysilane]; 3-[tris(trimethylsiloxy)silyl]propyl allyl carbamate; 3-[tris(trimethylsiloxy)wilyl]propyl vinyl carbamate; trimethylsilylethyl vinyl carbonate; trimethylsilylmethyl vinyl carbonate, and

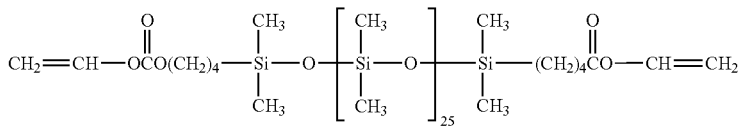

Another class of silicone-containing components includes compounds of the following formulae:

(*D*L*D*G)$_{aa}$*D*D*E$^1$;

E(*D*G*D*L)$_{aa}$*D*G*D*E$^1$ or;

E(*D*L*D*G)$_{aa}$*D*L*D*E$^1$    (Formulae XIII-XV)

wherein:
D denotes an alkyl diradical, an alkyl cycloalkyl diradical, a cycloalkyl diradical, an aryl diradical or an alkylaryl diradical having 6 to 30 carbon atoms,
G denotes an alkyl diradical, a cycloalkyl diradical, an alkyl cycloalkyl diradical, an aryl diradical or an alkylaryl diradical having 1 to 40 carbon atoms and which may contain ether, thio or amine linkages in the main chain;
* denotes a urethane or ureido linkage;
aa is an integer of at least 1;
L denotes a divalent polymeric radical of formula XVI:

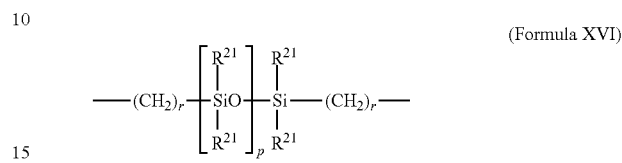

(Formula XVI)

in which $R^{21}$ independently denotes an alkyl or fluoro-substituted alkyl group having 1 to 10 carbon atoms which may contain ether linkages between carbon atoms; r is at least 1; and p provides a moiety weight of 400 to 10,000; each of E and $E^1$ independently denotes a polymerizable unsaturated organic radical represented by formula XVII:

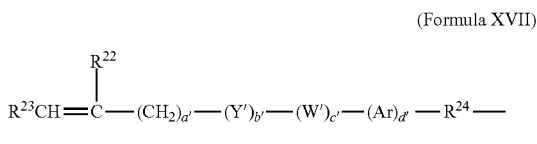

(Formula XVII)

wherein $R^{22}$ is hydrogen or methyl; $R^{23}$ is hydrogen, an alkyl radical having 1 to 6 carbon atoms, or a —CO—V'—$R^{25}$ radical wherein V' is —O—, —S— or —NH— and $R^{24}$ is hydrogen or an alkyl radical having 1 to 6 carbon atoms; $R^{24}$ is a divalent radical having 1 to 12 carbon atoms; Y' denotes —CO— or —OCO—; W' denotes —O— or —NH—; Ar denotes an aromatic radical having 6 to 10 carbon atoms; a' is 0 to 6; b' is 0 or 1; c' is 0 or 1; and d' is 0 or 1.

A preferred silicone-containing component is represented by the following formula XVIII:

(Formula XVIII)

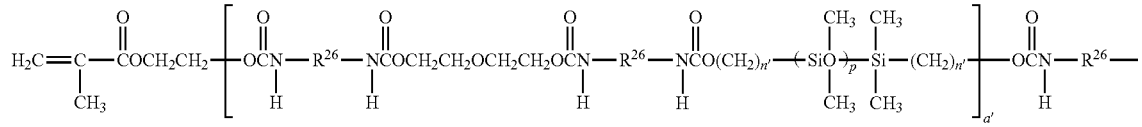

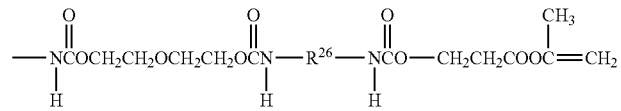

wherein $R^{26}$ is a diradical of a diisocyanate after removal of the isocyanate group, such as the diradical of isophorone diisocyanate. Another preferred silicone containing macromer is compound of formula XIX (in which x+y is a number in the range of 10 to 30) formed by the reaction of fluoroether, hydroxy-terminated polydimethylsiloxane, isophorone diisocyanate and isocyanatoethylmethacrylate.

$Y^3$ is a linker group;
$R^{24}$ is a $C_{1-12}$ alkyl group which may be optionally substituted with one or more $R^N$;
$G^1$ is a siloxane group-containing component;
Z is a zwitterionic group;
k is an integer from 1 to 10;
l is an integer from 1 to 3;

(Formula XIX)

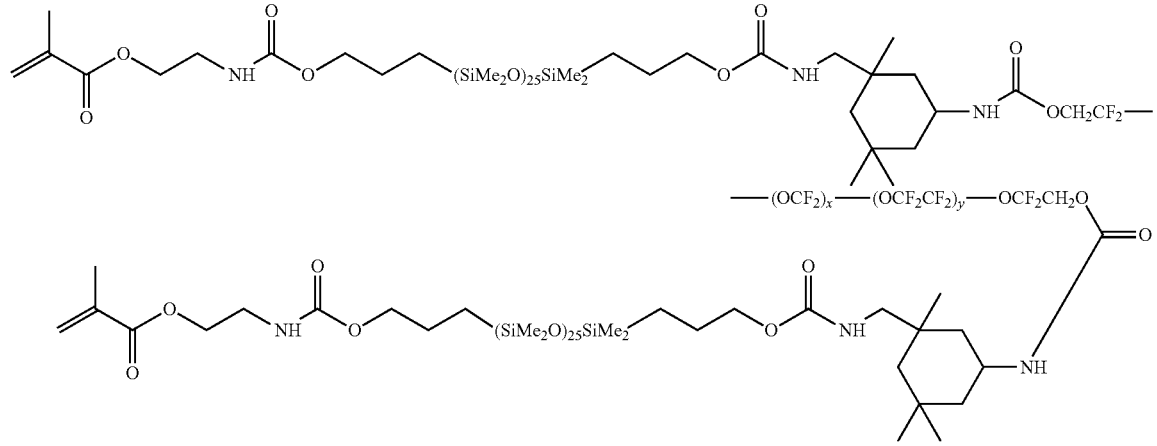

In an alternative embodiment of the present invention, the siloxane group-containing monomer may be a material of formula (A) or (B):

$(T^1-Y^1)_k-G^1(Y^2-Z)_l$ (A)

$[(T^1)_k-Y^3(Z)_u]_v-G^1-R^{24}$ (B)

wherein
$T^1$ is a polymerisable group;
$Y^1$ and $Y^2$ are each independently a linker group selected from the group consisting of a bond, $C_{1-12}$ alkylene, $C_{2-12}$ alkenylene, $C_{2-12}$ alkynylene, $C_{3-12}$ cycloalkylene, $C_{3-12}$ cycloalkenylene, $C_{2-12}$ heteroalkenylene, $C_{2-12}$ heteroalkynylene, arylene, heteroarylene, —C(O)—$C_{1-12}$ alkylene, —C(S)—$C_{1-12}$ alkylene, —C(O)O—$C_{1-12}$ alkylene, —C(O)S—$C_{1-12}$ alkylene, —C(O)N($R^M$)—$C_{1-12}$ alkylene, —C(S)—$C_{1-12}$ alkylene, —C(S) O—$C_{1-12}$ alkylene, —C(S)S—$C_{1-12}$ alkylene, —C(S)N ($R^M$)—$C_{1-12}$ alkylene, —$(CH_2)_{qq}(OCH_2CH_2)_{rr}$— and —$(CH_2CH_2O)_{rr}(CH_2)_{qq}$—, wherein $R^M$ is hydrogen or $C_{1-4}$ alkyl, qq is an integer from 1 to 10, rr is an integer from 1 to 10, wherein one or more carbon atoms in the $C_{1-12}$ alkylene group may be optionally replaced with a heteroatom selected from the group consisting of S and O and the alkylene, alkenylene, alkynylene, cycloalkylene, cycloalkenylene, heteroalkenylene, heteroalkynylene, arylene and heteroarylene groups may be optionally substituted with one or more $R^N$, wherein each $R^N$ is independently selected from the group consisting of —H, —OH, —CN, —NO$_2$, —CF$_3$, —OCF$_3$, —CO$_2$H, —NH$_2$, $C_1$-$C_{10}$ alkyl, $C_2$-$C_{10}$ alkenyl, $C_2$-$C_{10}$ alkynyl, —O($C_1$-$C_{10}$ alkyl), —O($C_2$-$C_{10}$ alkenyl), —O($C_2$-$C_{10}$ alkynyl), halogen, —C(O)H, —C(O)—($C_1$-$C_{10}$ alkyl), —C(O)—O($C_1$-$C_{10}$ alkyl), —NH($C_1$-$C_{10}$ alkyl), —N($C_1$-$C_{10}$alkyl)$_2$, —C(O)—NH($C_1$-$C_{10}$ alkyl), —C(O)—N($C_1$-$C_{10}$ alkyl)$_2$, —NH—C(O)—($C_1$-$C_{10}$ alkyl), —NH($C_1$-$C_{10}$ alkyl)-C(O)—($C_1$-$C_{10}$ alkyl), —NH—S(O)$_2$—($C_1$-$C_{10}$ alkyl), —NH—($C_1$-$C_{10}$ alkyl)-S(O)$_2$—($C_1$-$C_{10}$ alkyl), —($C_0$-$C_{10}$)—SH, —S(O)—($C_1$-$C_{10}$ alkyl), —S(O)$_2$—($C_1$-$C_{10}$ alkyl), —S(O)$_2$—NH$_2$, —S(O)$_2$—NH—($C_1$-$C_{10}$ alkyl), —S(O)$_2$—N($C_1$-$C_{10}$ alkyl)$_2$ and =O;

u is an integer from 1 to 3; and
v is an integer from 1 to 3.

In such embodiments of the present invention, the siloxane group-containing monomer includes a polymerisable group, siloxane functionality and a zwitterionic functionality within the same molecule. This is advantageous because any phase separation may be at a molecular level and so will not be visible to the naked eye. Furthermore, combining the functionalities on a molecular level makes it possible to provide materials which have a higher oxygen permeability than might be expected for a given water content.

Although formula (A) and formula (B) (and the chemical formulae which follow herein) are represented without any indication of specific stereochemistry, the skilled person will understand that a number of isomers are possible. In this regard, the present invention includes within its scope, all possible stereoisomers of the chemical structures depicted.

The polymerisable group $T^1$ is not limited and it may be any group which is capable of reaction under polymerisation conditions to form a polymer. It is the presence of the polymerisable group in the materials of the present invention which means that it is possible to form polymers and, ultimately, contact lenses from the materials of the present invention. In certain embodiments, the polymerisable group includes at least one carbon-carbon unsaturated bond. In such embodiments, the group is capable of addition polymerisation reactions. Alternatively, or in addition, the group which is capable of reaction to form a polymer is a multi-functionalised derivative which is capable of condensation polymerisation. This includes, for example, materials such as diols, diamines, diacids and derivatives thereof.

In one embodiment, the siloxane group-containing monomer is a material of formula (A). In an alternative embodiment, the siloxane group-containing monomer is a material of formula (B).

In one embodiment, the polymerisable group $T^1$ includes a group which is selected from the group consisting of acrylates, methacrylates, acrylamides, methacrylamides, styrenic and vinylic groups. Examples of suitable vinylic groups include allyl derivatives, N-vinyl lactam derivatives, such as suitably substituted N-vinyl pyrrolidone derivatives and N- and O-vinyl derivatives.

In one embodiment, the polymerisable group $T^1$ is a methacrylate or acrylate group. Preferably, the polymerisable group $T^1$ is a methacrylate group.

With reference to formula (A) and formula (B) above, k is an integer which defines the number of polymerisable groups, $T^1$, present in the polymerisable material. k may be 1, 2, 3, 4, 5, 6, 7, 8, 9 or 10. Preferably, k is 1 or 2.

Y' is a linker group which forms a link between the polymerisable group T' and the siloxane group-containing component, $G^1$, in a polymerisable material of formula (A). $Y^2$ is a linker group which forms a link between the siloxane group-containing component, $G^1$ and the zwitterionic group, Z in a polymerisable material of formula (A). $Y^1$ and $Y^2$ are each independently selected from the group consisting of a bond, $C_{1-12}$ alkylene, $C_{2-12}$ alkenylene, $C_{2-12}$ alkynylene, $C_{3-12}$ cycloalkylene, $C_{3-12}$ cycloalkenylene, $C_{2-12}$ heteroalkenylene, $C_{2-12}$ heteroalkynylene, arylene, heteroarylene, —C(O)—$C_{1-12}$ alkylene, —C(S)—$C_{1-12}$ alkylene, —C(O)O—$C_{1-12}$ alkylene, —C(O)S—$C_{1-12}$ alkylene, —C(O)N($R^M$)—$C_{1-12}$ alkylene, —C(S)—$C_{1-12}$ alkylene, —C(S)O—$C_{1-12}$ alkylene, —C(S)S—$C_{1-12}$ alkylene, —C(S)N($R^M$)—$C_{1-12}$ alkylene, —$(CH_2)_{qq}(OCH_2CH_2)_{rr}$— and —$(CH_2CH_2O)_{rr}(CH_2)_{qq}$—, wherein $R^M$ is hydrogen or $C_{1-4}$ alkyl, qq is an integer from 1 to 10, rr is an integer from 1 to 10, wherein one or more carbon atoms in the $C_{1-12}$ alkylene group may be optionally replaced with a heteroatom selected from the group consisting of S and O and the alkylene, alkenylene, alkynylene, cycloalkylene, cycloalkenylene, heteroalkenylene, heteroalkynylene, arylene and heteroarylene groups may be optionally substituted with one or more $R^N$, wherein each $R^N$ is independently selected from the group consisting of —H, —OH, —CN, —$NO_2$, —$CF_3$, —$OCF_3$, —$CO_2H$, —$NH_2$, $C_1$-$C_{10}$ alkyl, $C_2$-$C_{10}$ alkenyl, $C_2$-$C_{10}$ alkynyl, —O($C_1$-$C_{10}$ alkyl), —O($C_2$-$C_{10}$ alkenyl), —O($C_2$-$C_{10}$ alkynyl), halogen, —C(O)H, —C(O)—($C_1$-$C_{10}$ alkyl), —C(O)—O($C_1$-$C_{10}$ alkyl), —NH($C_1$-$C_{10}$ alkyl), —N($C_1$-$C_{10}$ alkyl)$_2$, —C(O)—NH($C_1$-$C_{10}$ alkyl), —C(O)—N($C_1$-$C_{10}$ alkyl)$_2$, —NH—C(O)—($C_1$-$C_{10}$ alkyl), —NH($C_1$-$C_{10}$ alkyl)-C(O)—($C_1$-$C_{10}$ alkyl), —NH—S(O)$_2$—($C_1$-$C_{10}$ alkyl), —NH—($C_1$-$C_{10}$ alkyl)-S(O)$_2$—($C_1$-$C_{10}$ alkyl), —($C_0$-$C_{10}$)—SH, —S(O)—($C_1$-$C_{10}$ alkyl), —S(O)$_2$—($C_1$-$C_{10}$ alkyl), —S(O)$_2$—($C_1$-$C_{10}$ alkyl), —S(O)$_2$—$NH_2$, —S(O)$_2$—NH—($C_1$-$C_{10}$ alkyl), —S(O)$_2$—N($C_1$-$C_{10}$ alkyl)$_2$ and =O. $Y^1$ and $Y^2$ may be the same or different. In one embodiment, $Y^1$ and $Y^2$ are the same. In an alternative embodiment, $Y^1$ and $Y^2$ are different.

In one embodiment, $Y^1$ and $Y^2$ are each independently a $C_{1-12}$ alkylene group. In an alternative embodiment, $Y^1$ is a group of formula —$(CH_2)_q(OCH_2CH_2)_r$— and $Y^2$ is a group of formula —$(CH_2CH_2O)_{rr}(CH_2)_{qq}$—, wherein rr is an integer in the range from 1 to 10, preferably 4 to 6 and qq is an integer in the range from 1 to 10, in one embodiment, 2 to 4, preferably 3.

$Y^3$ is a linker group which forms a link between the polymerisable group, $T^1$ and the siloxane group, $G^1$, in polymerisable material of formula (B). In this embodiment of the present invention, the zwitterionic group, Z, is a substituent on the linker group, $Y^3$. The nature of $Y^3$ is not particularly limited and in a preferred embodiment, $Y^3$ is selected from the group consisting of a bond, $C_{1-12}$ alkylene, $C_{2-12}$ alkenylene, $C_{2-12}$ alkynylene, $C_{3-12}$ cycloalkylene, $C_{3-12}$ cycloalkenylene, $C_{1-12}$ heteroalkylene, $C_{2-12}$ heteroalkenylene, $C_{2-12}$ heteroalkynylene, arylene, heteroarylene, —C(O)—, —C(S)—, —C(O)O—, —C(O)S—, —C(O)N($R^M$)—, —C(S)—, —C(S)O—, —C(S)S— and —C(S)N($R^M$)—, wherein $R^M$ is hydrogen or $C_{1-4}$ alkyl. The alkylene, alkenylene, alkynylene, cycloalkylene, cycloalkenylene, heteroalkenylene, heteroalkynylene, arylene and heteroarylene groups may be optionally substituted with one or more $R^N$, wherein each $R^N$ is independently selected from the group consisting of —H, —OH, —CN, —$NO_2$, —$CF_3$, —$OCF_3$, —$CO_2H$, —$NH_2$, $C_1$-$C_{10}$ alkyl, $C_2$-$C_{10}$ alkenyl, $C_2$-$C_{10}$ alkynyl, —O($C_1$-$C_{10}$ alkyl), —O($C_2$-$C_{10}$ alkenyl), —O($C_2$-$C_{10}$ alkynyl), halogen, —C(O)H, —C(O)—($C_1$-$C_{10}$ alkyl), —C(O)—O($C_1$-$C_{10}$ alkyl), —NH($C_1$-$C_{10}$ alkyl), —N($C_1$-$C_{10}$ alkyl)$_2$, —C(O)—NH($C_1$-$C_{10}$ alkyl), —C(O)—N($C_1$-$C_{10}$ alkyl)$_2$, —NH—C(O)—($C_1$-$C_{10}$ alkyl), —NH($C_1$-$C_{10}$ alkyl)-C(O)—($C_1$-$C_{10}$ alkyl), —NH—S(O)$_2$—($C_1$-$C_{10}$ alkyl), —NH—($C_1$-$C_{10}$ alkyl)-S(O)$_2$—($C_1$-$C_{10}$ alkyl), —($C_0$-$C_{10}$)—SH, —S(O)—($C_1$-$C_{10}$ alkyl), —S(O)$_2$—($C_1$-$C_{10}$ alkyl), —S(O)$_2$—$NH_2$, —S(O)$_2$—NH—($C_1$-$C_{10}$ alkyl), —S(O)$_2$—N($C_1$-$C_{10}$ alkyl)$_2$ and =O. The position of the group Z as a substituent of the linker group $Y^3$ is not limited. In this regard, the group Z may be a substituent on any one of the carbon atoms which form a part of the backbone of the linker group, $Y^3$.

In one embodiment, $Y^3$ is a $C_{1-12}$ alkylene or heteroalkylene group, in particular a heteroalkylene group of formula —$(CH_2)_{qq}(OCH_2CH_2)_{rr}$— or —$(CH_2CH_2O)_{rr}(CF_{12})_{qq}$—, wherein qq is an integer from 1 to 10 and rr is an integer from 1 to 10. In a preferred embodiment, $Y^3$ is —$(CH_2)_3$—O—$(CH_2)_3$—. In a preferred embodiment of the present invention, the position of substitution of the Z group on the $Y^3$ group is such that the group —$Y^3$(Z)— is —$(CH_2CH(Z)CH_2)$—O—$(CH_2)_3$—.

$G^1$ is the siloxane group-containing component of the siloxane-group containing monomer of this embodiment. As described previously, it is the inclusion of the siloxane functionality in the siloxane group-containing monomer which provides a material which has good gas permeability. The nature of the siloxane group-containing component is not particularly limited and the skilled person will be familiar with suitable components. A siloxane group is one which includes the residue having the general structure —[Si(R)$_2$O]—, wherein each R is independently selected from hydrogen or a $C_{1-12}$ alkylene, $C_{2-12}$ alkenylene, $C_{2-12}$ alkynylene, $C_{3-12}$ cycloalkylene, $C_{3-12}$ cycloalkenylene, $C_{1-12}$ heteroalkylene, $C_{2-12}$ heteroalkenylene, $C_{2-12}$ heteroalkynylene, arylene, heteroarylene group, optionally substituted with one or more $R^N$, wherein each $R^N$ is independently selected from the group consisting of —H, —OH, —CN, —$NO_2$, —$CF_3$, —$OCF_3$, —$CO_2H$, —$NH_2$, $C_1$-$C_{10}$ alkyl, $C_2$-$C_{10}$ alkenyl, $C_2$-$C_{10}$ alkynyl, —O($C_1$-$C_{10}$ alkyl), —O($C_2$-$C_{10}$ alkenyl), —O($C_2$-$C_{10}$ alkynyl), halogen, —C(O)H, —C(O)—($C_1$-$C_{10}$ alkyl), —C(O)—O($C_1$-$C_{10}$ alkyl), —NH($C_1$-$C_{10}$ alkyl), —N($C_1$-$C_{10}$ alkyl)$_2$, —C(O)—NH($C_1$-$C_{10}$ alkyl), —C(O)—N($C_1$-$C_{10}$ alkyl)$_2$, —NH—C(O)—($C_1$-$C_{10}$ alkyl), —NH($C_1$-$C_{10}$ alkyl)-C(O)—($C_1$-$C_{10}$ alkyl), —NH—S(O)$_2$—($C_1$-$C_{10}$ alkyl), —NH—($C_1$-$C_{10}$ alkyl)-S(O)$_2$—($C_1$-$C_{10}$ alkyl), —($C_0$-$C_{10}$)—SH, —S(O)—($C_1$-$C_{10}$ alkyl), —S(O)$_2$—($C_1$-$C_{10}$ alkyl), —S(O)$_2$—$NH_2$, —S(O)$_2$—NH—($C_1$-$C_{10}$ alkyl), —S(O)$_2$—N($C_1$-$C_{10}$ alkyl)$_2$ and =O. The R groups may be the same or different. In one embodiment all of the R groups are the same. In an alternative embodiment, the R groups are different. Preferably R is a $C_{1-12}$ alkylene group, preferably a $C_{1-6}$ alkylene group. Preferably, the Si and attached O are present in the siloxane group in an amount greater than 20 weight percent, and more preferably greater than 30 weight percent of the total molecular weight of the siloxane group-containing component.

In one embodiment, the siloxane group-containing component has the formula (a):

(a)

wherein R is as defined previously and w is an integer from 1 to 500.

In one embodiment, the siloxane group-containing component has the formula (b):

(b)

wherein R is as defined previously and $w^1$ and $w^2$ are independently an integer in the range from 1 to 500.

In one embodiment, the siloxane group-containing component has the formula (c):

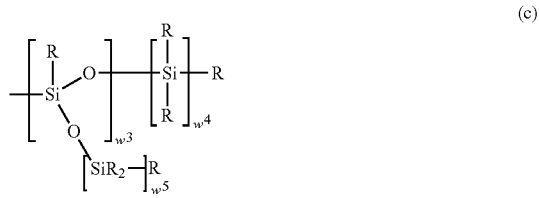

(c)

wherein R is as defined previously and $w^3$, $w^4$ and $w^5$ are each independently an integer in the range from 1 to 500.

In one embodiment, the siloxane group-containing component has the formula (d):

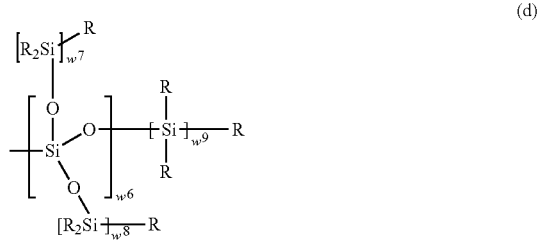

(d)

wherein R is as defined previously and $w^6$, $w^7$, $w^8$ and $w^9$ are each independently an integer in the range from 1 to 500.

Z is a zwitterionic group as defined previously. Where the siloxane group-containing monomer has formula (A), Z is bonded to $Y^2$. Where the siloxane group-containing monomer has formula (B), Z is a substituent on the linker group $Y^3$.

Preferably, Z is a group of formula (IIB), in particular, a group of formula (IIB), wherein all $R^4$ groups are methyl groups and b is 2. In this embodiment, the zwitterionic group is a phosphorylcholine (PC) group.

l is an integer which defines the number of zwitterionic groups which are present in the siloxane group-containing monomer of formula (A). l may be 1, 2 or 3. Preferably, l is 1 or 2.

u is an integer which defines the number of zwitterionic groups which are present in the siloxane group-containing monomer of formula (B). u may be 1, 2 or 3. Preferably, u is 1 or 2.

v is an integer which defines the number of $[(T^1)_k\text{-}Y^3(Z)_u]$ groups which are present in the siloxane group-containing monomer of formula (B). u may be 1, 2 or 3. Preferably, u is 1 or 2.

Exemplary Siloxane Group-Containing Monomers of Formula (A)

In one embodiment, the siloxane group-containing monomer of the present invention has the formula (AA):

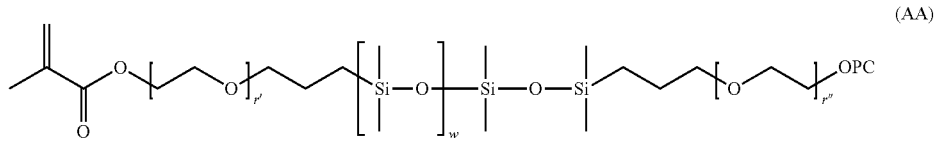

(AA)

wherein "OPC" is a zwitterionic group of formula (IIB), wherein all $R^4$ groups are methyl and b is 2, w is an integer from 1 to 500, r' and r" may be the same or different and are each independently an integer from 0 to 10, preferably 4 to 6.

Accordingly, in one embodiment, the siloxane group-containing monomer is a material of formula (A), wherein $T^1$ is a methacrylate group, $Y^1$ is $(CH_2CH_2O)_{r'}(CH_2)_3$, $G^1$ is a group of formula (c), w is an integer from 1 to 500, $Y^2$ is $(CH_2)_3(CH_2CH_2O)_{r''}$, Z is a group of formula (IIB) wherein all $R^4$ groups are methyl and b is 2, k is 1, l is 1 and r' and r" may be the same or different and are each independently an integer between 0 and 10, preferably 4 to 6.

In one embodiment of the invention, the polymerisable material is a material of formula (AB):

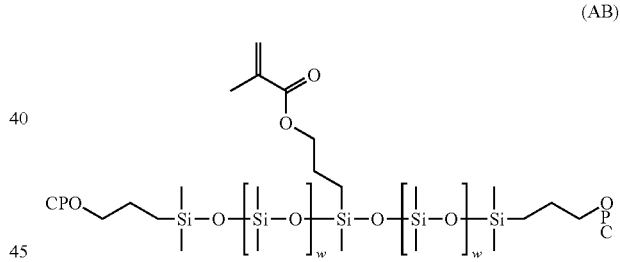

(AB)

wherein "OPC" is a zwitterionic group of formula (IIB), wherein all $R^4$ groups are methyl and b is 2 and w is 0 to 15.

Accordingly, in one embodiment, the siloxane group-containing monomer is a material of formula (A), wherein $T^1$ is a methacrylate group, $Y^1$ is $(CH_2)_3$, w is 0 to 15, preferably 2 to 4, $Y^2$ is $(CH_2)_3$, Z is a group of formula (IIB) wherein all $R^4$ groups are methyl and b is 2, k is 1 and l is 2.

Exemplary Siloxane Group-Containing Monomers of Formula (B)

In one embodiment of the present invention, the polymerisable monomer of the present invention has the formula (BB):

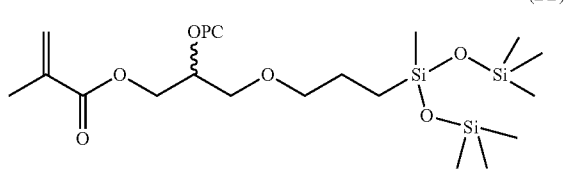

(BB)

wherein "OPC" is a zwitterionic group of formula (IIB), wherein all $R^4$ groups are methyl and b is 2.

Accordingly, in one embodiment, the siloxane group-containing monomer is a material of formula (B), wherein $T^1$ is a methacrylate group, $Y^3$ is —$(CH_2)_3$—O—$(CH_2)_3$—, Z is a group of formula (JIB) wherein all $R^4$ groups are methyl and b is 2, W is a group of formula (c), $R^{24}$ is methyl, u is 1 and v is 1.

In an alternative embodiment of the present invention, the siloxane group-containing monomer has the formula (BC).

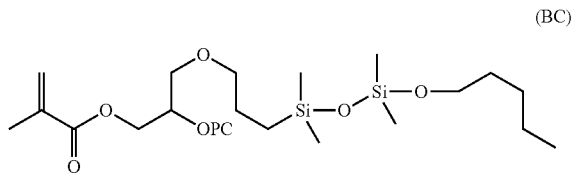

(BC)

wherein "OPC" is a zwitterionic group of formula (IIB), wherein all $R^4$ groups are methyl and b is 2.

Accordingly, in one embodiment, the siloxane group-containing monomer is a material of formula (B), wherein $T^1$ is a methacrylate group, $Y^3$ is —$(CH_2)_3$—O—$(CH_2)_3$—, Z is a group of formula (IIB), wherein all $R^4$ groups are methyl and b is 2, $G^1$ is a group of formula (a), $R^{24}$ is $(CH_2)_4CH_3$, u is 1 and v is 1.

In one embodiment the siloxane group-containing monomer has the formula (BD):

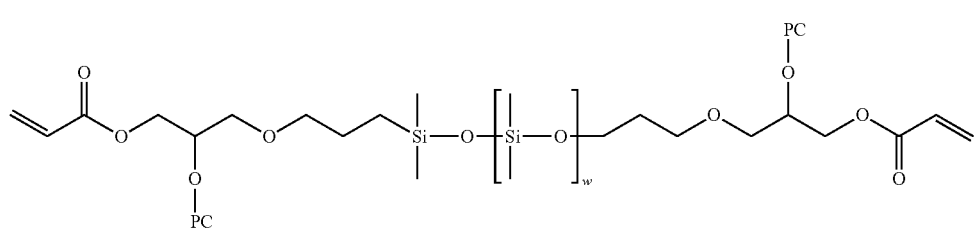

(BD)

wherein "OPC" is a zwitterionic group of formula (JIB), wherein all $R^4$ groups are methyl and b is 2 and w is an integer from 1 to 500.

Accordingly, in one embodiment, the siloxane group-containing monomer is a material of formula (B), wherein T' is an acrylate group, $Y^3$ is —$(CH_2)$—$(CH(OZ))$—$CH_2$—O—$(CF_{12})_3$—, Z is a group of formula (IIB), wherein all $R^4$ groups are methyl and b is 2, $G^1$ is a group of formula (a), $R^{24}$ is methyl, u is 1 and v is 2.

Other silicone-containing components suitable for use in this invention include those described in WO 96/31792 such as macromers containing polysiloxane, polyalkylene ether, diisocyanate, polyfluorinated hydrocarbon, polyfluorinated ether and polysaccharide groups. U.S. Pat. No. 5,321,108, U.S. Pat. No. 5,387,662 and U.S. Pat. No. 5,539,016 all describe polysiloxanes with a polar fluorinated graft or side group having a hydrogen atom attached to a terminal difluoro-substituted carbon atom. Such polysiloxanes may also be used as the siloxane group-containing monomer in the co-solvent system.

Alternatively, the siloxane group-containing monomer may be a hydroxyl-functionalised siloxane group-containing monomer. Examples include 2-methyl-2-hydroxy-3-[3-[1,3,3,3-tetramethyl-1-[trimethylsilyl)oxy]disiloxanyl]propoxy] propyl ester (which can also be named (3-methacryloxy-2-hydroxypropyloxy)propylbis(trimethylsiloxy)methylsilane), 3-methacryloxy-2-hydroxypropyloxy)propyltris(trimethylsiloxy)silane, bis-3-methacryloxy-2-hydroxypropyloxypropyl polydimethylsiloxane, 3-methacryloxy-2-(2-hydroxyethoxy)propyloxy)propylbis(trimethylsiloxy)methylsilane, N-2-methacryloxyethyl-O-(methyl-bis-trimethylsiloxy-3-propyl)silyl carbamate and N,N,N',N'-tetrakis(3-methacryloxy-2-hydroxypropyl)-[alpha],[omega]-bis-3-aminopropyl-polydimethylsiloxane and mixtures thereof.

In one embodiment, the siloxane group-containing monomer is selected from the group consisting of 3-[Tris(trimethylsiloxy)silyl]propyl methacrylate, methacryloxypropyl terminated polydimethylsiloxane; monomethacryloxypropyl functional polydimethylsiloxane; monomethacryloxypropyl terminated polytrifluoropropylmethyl-siloxane-symmetric, 2-hydroxy-3-[3-[1,3,3,3-tetramethyl-1-[(trimethylsilyl)oxy] disiloxanyl]propoxy]propyl methacrylate and tristrimethylsiloxysilyl propylvinyl carbamate.

In one embodiment, the polymers of the present invention are obtainable by reacting about 1 to 100 mol % monomer of formula (I) with about 1 to about 95 mol % siloxane monomer and other diluent monomers to a total of 100%. The diluent monomers may be monomers which comprise a vinyl group, including but not limited to acrylates, methacrylates such as methacrylic acid, methylmethacrylate, hydroxyethylmethacrylate, acrylamides such as dimethylacrylamide, N-vinyl lactams, such as N-vinylpyrrolidone, and N- and O-vinyl derivatives such as hydroxyethylvinylcarbamate, hydroxyethylvinylcarbonate In the polymers of the present invention, a monomer of formula (I) preferably accounts for about 1 to 100%, alternatively about 1 to about 80%, alternatively about 2 to about 70%, alternatively about 3 to about 60%, alternatively about 4 to about 50%, alternatively about 5 to about 40% by weight based on the total polymer.

In one embodiment, the co-monomer system with which the monomers of the present invention are reacted comprises a co-monomer which comprises a vinyl group. In one embodiment, the co-monomer which comprises a vinyl group is one in which the vinyl group is directly attached to a heteroatom.

Advantageously, for a copolymerisation reaction to be effective, the reactivity rates of the two co-monomers need to be closely matched. Thus, as the monomers of the present invention include a terminal vinyl group, it is possible to generate a whole new class of polymers which include a zwitterionic functionality, because it enables vinyl systems of differing reactivity, which are useful in ophthalmic applications, to be used as co-monomers in place or together with acrylic monomers. These polymer products cannot be produced using the presently used methacrylate monomers, such as MPC, due to solubility issues and the difference in reaction rate between methacrylate and vinyl systems.

Where the polymers of the present invention have been obtained by reaction with a comonomer system which includes a siloxane monomer, as a consequence of the presence of the terminal vinyl group, the zwitterionic group and the siloxane functionality, the polymers of the present invention are particularly useful in the manufacture of ophthalmic lenses, in particular contact lenses.

Therefore, in a further aspect, the present invention provides an article, in particular an ocular device, comprising a polymer as defined herein. Preferably, the ocular device is an ophthalmic lens, preferably a contact lens.

An ophthalmic lens is a lens which, in use, will be placed in intimate contact with the eye or tear fluid. The term "ophthalmic lens" is intended to include contacts lenses for vision correction, contact lenses for changing eye colour, ophthalmic drug delivery devices and ocular tissue protective devices.

The ophthalmic lenses of the present invention may be manufactured by applying an appropriate amount of a mixture of a monomer of the present invention and the co-monomer system with which it is to be reacted to a lens mold cavity and initiating polymerization. Initiators, including photoinitiators, which are commercially available may be added to the mixture to aid initiation of the polymerization. As described previously, polymerization may be initiated by a number of well known techniques depending on the exact nature of the mixture. Examples of suitable techniques include application of radiation such as microwave, e-beam or ultraviolet. Alternatively, polymerization may be initiated by heating.

In contrast to other tissues which receive oxygen from blood flow, the cornea receives oxygen primarily from the corneal surface which is exposed to the environment. Therefore, an ophthalmic lens which is intended to be worn on the eye for extended periods of time must allow sufficient oxygen to permeate through the lens in order to sustain corneal health. It is possible to detect when the cornea has received an inadequate supply of oxygen because it will swell. Preferably, the oxygen permeability of the ophthalmic lenses of the present invention is sufficient to prevent any clinically significant swelling of the cornea from occurring. In one embodiment, the extent of corneal swelling observed is about 10% or less over at least 8 hours, about 8% or less over at least 8 hours, about 6% or less over at least 8 hours, about 4% or less over at least 8 hours, about 2% or less over at least 8 hours, about 1% or less over at least 8 hours.

In this regard, preferably an ophthalmic lens of the present invention is suitable for extended wear. Advantageously, the ophthalmic lenses of the present invention may be worn by a user for up to 4 days or more, in one embodiment 7 days or more, in one embodiment 14 days or more, in one embodiment 30 days or more, without causing substantial corneal damage or user discomfort.

Accordingly, in one embodiment, the article of the present invention has an oxygen permeability of about 20 barriers or more, alternatively about 30 barriers or more, alternatively about 40 barriers or more, alternatively about 50 barriers or more, preferably about 60 barriers or more.

In one embodiment, the polymer of the present invention has an equilibrium water content of 10% or more, 15% or more, 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 95% or more. In one embodiment, the water content of the polymer is in the range from about 20 to about 60%, preferably about 30 to about 50%.

Alternatively or in addition, the polymers of the present invention may have a tensile modulus (modulus of elasticity, E) of less than about 3 MPa. In one embodiment, the tensile modulus is in the range from 0.2 to about 2.5 MPa, in one instance about 0.3 to 1.5 MPa, preferably about 0.4 to about 1 MPa.

Alternatively or in addition, the articles of the present invention may have an optical transmission of about 80% or more, about 85% or more, about 90% or more, about 95% or more, about 99% or more. In a preferred embodiment, the articles of the present invention are transparent and/or clear which is particularly advantageous where the article is an ocular device.

Alternatively or in addition, the articles of the present invention may have a % of scattered visible light (haze) of <100%, in one embodiment, <80%, in one embodiment, <60%, in one embodiment <50%, measured according to the standard ASTM D 1003.

In one embodiment, the polymers of the present invention may be used to biocompatibilise a surface. Thus, in a further aspect, the present invention provides a process for biocompatibilising a surface comprising coating the surface with a polymer of the present invention. The invention further provides an article comprising a surface having coated thereon a polymer as defined herein. The polymers of the present invention may be used to coat many different surfaces, depending on the nature of the groups which are present in the polymer and capable of binding it to the surface.

Coating of a surface with the polymer may generally be carried out by coating the surface with a solution or dispersion of the polymer, generally in an alcoholic, aqueous, organic or halogenated solvent or a mixture thereof. Examples of suitable solvents include methanol, ethanol, dichloromethane and freon. Coating may be carried out at room temperature or at an elevated temperature. Generally, coating is carried out at a temperature in the range from 5 to 60° C.

Surfaces may be coated with the polymers of the present invention by known techniques, such as dip-coating, spray-coating, web-coating or spin coating.

In one embodiment, the polymer is coated onto the surface in the form of a microdispersion, such as a microemulsion.

After coating, where the polymer of the present invention includes cross-linkable groups, it may be subjected to a cross-linking reaction. The cross-linking may be carried out by known methods, for example thermally, using actinic radiation, using reactive gases, for example ammonia, by changing the pH, using difunctional additives or by using activation chemistries, for example by known methods as described in "Methods in Enzymology, volume 135, Immobilised Enzymes and Cells, part B", Ed. K. Mosbach, Academic Press Inc., New York, 1987. In cases where crosslinking is achieved thermally or by gas treatment, the treatment may be carried out on the dried coating. Alternatively, where the pH needs to be changed or additives need to be included, treatment may be performed on the coated material in a solution which does not remove the coating. In some embodiments, crosslinking may be carried out with the coating hydrated which facilitates the crosslinking reaction.

The polymers of the present invention may be used to coat a surface of materials which can be used as a construction material for implants or prostheses for the human or animal body, particularly where these implants or prostheses have direct physical contact with blood and where biocompatibility and haemocompatibility are required. They can also be used in the construction of membranes and other devices that are to be brought into contact with blood or other body fluids on an extra-corporeal basis, for example in heart-lung machines or artificial kidneys.

The polymers of the present invention may also be used to coat materials used in processing applications, for example separation membranes and process equipment and tubing. In particular, the polymers of the present invention may be used to modify the surface properties of biofiltration membranes in bioreactors and fermentation systems where the membranes come into direct contact with complex biological solutions containing e.g. proteins, polysaccharides, fats and whole cells. The polymers of the present invention may be useful in reducing membrane fouling by components of a process solution.

When the polymers of the present invention are used to coat the surface of a material which is then used in the construction coat of finished devices, it may be necessary to take precautionary steps to ensure that the coated surface is not damaged and the effectiveness of the treatment reduced before the finished device is produced.

The polymers of the present invention may be used to coat finished implants, prostheses, membranes, catheters, contact lenses, intraocular lenses, and other devices to impart biocompatibility to the article.

Therefore, in a further aspect, the present invention provides an article comprising a surface having a coating thereon of a polymer of the present invention.

In one embodiment, the article is an ocular device, in particular an ophthalmic lens, in particular a contact lens.

Several illustrative embodiments of the invention are described by the following enumerated clauses:

1. A monomer of formula (I):

$$\text{(I)} \quad \underset{W}{\overset{R^1}{\diagdown}}\text{--X--Y--}(CR^1{}_2)_m\text{--Z}$$

wherein:
W is $(CR^1{}_2)_n$;
X is O, S or $NR^2$;
Y is a linker group;
Z is a zwitterionic group;
each $R^1$ is independently selected from H, halogen or $C_{1-4}$ alkyl;
$R^2$ is H or $C_{1-4}$ alkyl;
n is an integer from 0 to 6; and
m is an integer from 0 to 6.

2. A monomer according to clause 1, wherein Y is selected from the group consisting of $C_{1-10}$ alkylene, $C_{2-10}$ alkenylene, $C_{2-10}$ alkynylene, $C_{3-10}$ cycloalkylene, $C_{3-10}$ cycloalkenylene, $C_{1-10}$ heteroalkylene, $C_{2-10}$ heteroalkenylene, $C_{2-10}$ heteroalkynylene, arylene, heteroarylene, —C(O)—, —C(S)—, —C(O)O—, —C(O)S—, C(O)N($R^M$)—, —C(S)—, —C(S)O—, —C(S)S— and —C(S)N($R^M$)—, wherein $R^M$ is hydrogen or $C_{1-4}$ alkyl and wherein the alkylene, alkenylene, alkynylene, cycloalkylene, cycloalkenylene, heteroalkylene, heteroalkenylene, heteroalkynylene, arylene and heteroarylene groups may be optionally substituted with one or more $R^N$, wherein each $R^N$ is independently selected from the group consisting of —H, —OH, —CN, —NO$_2$, —CF$_3$, —OCF$_3$, —CO$_2$H, —NH$_2$, $C_1$-$C_{10}$ alkyl, $C_2$-$C_{10}$ alkenyl, $C_2$-$C_{10}$ alkynyl, —O($C_1$-$C_{10}$ alkyl), —O($C_2$-$C_{10}$ alkenyl), —O($C_2$-$C_{10}$ alkynyl), halogen, —C(O)H, —C(O)—($C_1$-$C_{10}$ alkyl), —C(O)—O($C_1$-$C_{10}$ alkyl), —NH($C_1$-$C_{10}$ alkyl), —N($C_1$-$C_{10}$ alkyl)$_2$, —C(O)—NH($C_1$-$C_{10}$ alkyl), —C(O)—N($C_1$-$C_{10}$ alkyl)$_2$, —NH—C(O)—($C_1$-$C_{10}$ alkyl), —NH($C_1$-$C_{10}$ alkyl)-C(O)—($C_1$-$C_{10}$ alkyl), —NH—S(O)$_2$—($C_1$-$C_{10}$ alkyl), —NH—($C_1$-$C_{10}$ alkyl)-S(O)$_2$—($C_1$-$C_{10}$ alkyl), —($C_0$-$C_{10}$)—SH, —S(O)—($C_1$-$C_{10}$ alkyl), —S(O)$_2$—($C_1$-$C_{10}$ alkyl), —S(O)$_2$—NH$_2$, —S(O)$_2$—NH—($C_1$-$C_{10}$ alkyl), —S(O)$_2$—N($C_1$-$C_{10}$ alkyl)$_2$ and =O.

3. A monomer according to clause 1, wherein X is O.

4. A monomer according to clause 1, wherein X is $NR^2$.

5. A monomer according to clause 4, wherein $R^2$, Y and the N atom to which they are bonded taken together form a 5 to 7 membered heterocyclic ring, wherein the heterocyclic ring may be optionally substituted with one or more $R^N$, wherein each $R^N$ is independently selected from the group consisting of —H, —OH, —CN, —NO$_2$, —CF$_3$, —OCF$_3$, —CO$_2$H, —NH$_2$, $C_1$-$C_{10}$ alkyl, $C_2$-$C_{10}$ alkenyl, $C_2$-$C_{10}$ alkynyl, —O($C_1$-$C_{10}$ alkyl), —O($C_2$-$C_{10}$ alkenyl), —O($C_2$-$C_{10}$ alkynyl), halogen, —C(O)H, —C(O)—($C_1$-$C_{10}$ alkyl), —C(O)—O($C_1$-$C_{10}$ alkyl), —NH($C_1$-$C_{10}$ alkyl), —N($C_1$-$C_{10}$ alkyl)$_2$, —C(O)—NH($C_1$-$C_{10}$ alkyl), —C(O)—N($C_1$-$C_{10}$ alkyl)$_2$, —NH—C(O)—($C_1$-$C_{10}$ alkyl), —NH($C_1$-$C_{10}$ alkyl)-C(O)—($C_1$-$C_{10}$ alkyl), —NH—S(O)$_2$—($C_1$-$C_{10}$ alkyl), —NH—($C_1$-$C_{10}$ alkyl)-S(O)$_2$—($C_1$-$C_{10}$ alkyl), —($C_0$-$C_{10}$)—SH, —S(O)—($C_1$-$C_{10}$ alkyl), —S(O)$_2$—($C_1$-$C_{10}$ alkyl), —S(O)$_2$—NH$_2$, —S(O)$_2$—NH—($C_1$-$C_{10}$ alkyl), —S(O)$_2$—N($C_1$-$C_{10}$ alkyl)$_2$ and =O.

6. A monomer according to clause 5, wherein $R^2$, Y and the N atom to which they are bonded taken together from a 5-membered heterocyclic ring.

7. A monomer according to clause 6, wherein the 5-membered heterocyclic ring is substituted with =O.

8. A monomer according to clause 7, which has the formula (IA):

$$\text{(IA)}$$

wherein W, $R^1$, $R^2$ and Z as defined for formula (I).

9. A monomer according to clause 8, wherein n is 0.

10. A monomer according to any one of clauses 1 to 4, wherein Y is —C(O)O— and m is 1 to 4.

11. A monomer according to clause 10, wherein m is 2.

12. A monomer according to any one of clauses 1 to 8, wherein m is 0.

13. A monomer according to any preceding clause, wherein Z is a zwitterionic group selected from the group consisting of (IIA), (IIB), (IIC), (IID) and (IIE), wherein group (IIA) has the formula:

$$\text{(IIA)} \quad \underset{R_3}{\overset{R_3}{\mid}}\!\!-\!\!N^+\!\!-\!\!(CR^{3A}{}_2)_a\!\!-\!\!SO_3$$

wherein each $R^3$ and $R^{3A}$ is independently selected from hydrogen and $C_{1-4}$ alkyl and a is an integer from 2 to 4; group (IIB) has the formula:

$$\text{(IIB)} \quad -\!\!O\!\!-\!\!\overset{O}{\underset{O^\ominus}{\overset{\|}{P}}}\!\!-\!\!O\!\!-\!\!(CR^{4A}{}_2)_b\!\!-\!\!\overset{\oplus}{N}(R^4)_3$$

wherein each $R^4$ and $R^{4A}$ is independently selected from hydrogen and $C_{1-4}$ alkyl and b is an integer from 1 to 4; group (IIC) has the formula:

$$\text{(IIC)}$$

wherein each $R^5$ and $R^{5C}$ is independently selected from hydrogen and $C_{1-4}$ alkyl; $R^{5A}$ is hydrogen or a group —C(O)$B^1R^{5B}$, wherein $R^{5B}$ is hydrogen or methyl, $B^1$ is selected from the group consisting of a bond; $C_{1-10}$ alkylene, $C_{2-10}$ alkenylene, $C_{2-10}$ alkynylene, $C_{3-10}$ cycloalkylene, $C_{3-10}$ cycloalkenylene, $C_{1-10}$ heteroalkylene, $C_{2-10}$ heteroalkenylene, $C_{2-10}$ heteroalkynylene, arylene, heteroarylene, —C(O)$R^M$—, —C(O)O$R^M$—, wherein $R^M$ is selected from the group consisting of $C_{1-10}$ alkylene, $C_{2-10}$ alkenylene and $C_{2-10}$ alkynylene, and wherein the alkylene, alkenylene, alkynylene, cycloalkylene, cycloalkenylene, heteroalkylene, heteroalkenylene, heteroalkynylene, arylene and heteroarylene groups may be optionally substituted with one or more $R^N$, wherein each $R^N$ is independently selected from the group consisting of —H, —OH, —CN, —NO$_2$, —CF$_3$, —OCF$_3$, —CO$_2$H, —NH$_2$, $C_1$-$C_{10}$ alkyl, $C_2$-$C_{10}$ alkenyl, $C_2$-$C_{10}$ alkynyl, —O($C_1$-$C_{10}$ alkyl), —O($C_2$-$C_{10}$ alkenyl), —O($C_2$-$C_{10}$ alkynyl), halogen, —C(O)H, —C(O)—($C_1$-$C_{10}$ alkyl), —C(O)—O($C_1$-$C_{10}$ alkyl), —NH($C_1$-$C_{10}$ alkyl), —N($C_1$-$C_{10}$ alkyl)$_2$, —C(O)—NH($C_1$-$C_{10}$ alkyl), —C(O)—N($C_1$-$C_{10}$ alkyl)$_2$, —NH—C(O)—($C_1$-$C_{10}$ alkyl), —NH($C_1$-$C_{10}$ alkyl)-C(O)—($C_1$-$C_{10}$ alkyl), —NH—S(O)$_2$—($C_1$-$C_{10}$ alkyl), —NH—($C_1$-$C_{10}$ alkyl)-S(O)$_2$—($C_1$-$C_{10}$ alkyl), —($C_0$-$C_{10}$)—SH, —S(O)—($C_1$-$C_{10}$ alkyl), —S(O)$_2$—($C_1$-$C_{10}$ alkyl), —S(O)$_2$—NH$_2$, —S(O)$_2$—NH—($C_1$-$C_{10}$ alkyl), —S(O)$_2$—N($C_1$-$C_{10}$ alkyl)$_2$ and =O, and c is an integer from 1 to 4, wherein if Z is directly bonded to an O or N atom, z is 0 and otherwise z is 1;

group (IID) has the formula:

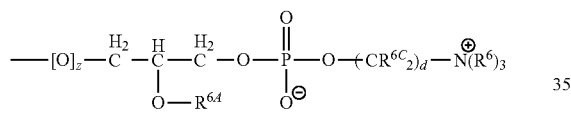

(IID)

wherein each $R^6$ and $R^{6C}$ is independently selected from hydrogen and $C_{1-4}$ alkyl; $R^{6A}$ is hydrogen or a group —C(O)B$^2R^{6B}$, wherein $R^{6B}$ is hydrogen or methyl, B$^2$ is selected from the group consisting of a bond; $C_{1-10}$ alkylene, $C_{2-10}$ alkenylene, $C_{2-10}$ alkynylene, $C_{3-10}$ cycloalkylene, $C_{3-10}$ cycloalkenylene, $C_{1-10}$ heteroalkylene, $C_{2-10}$ heteroalkenylene, $C_{2-10}$ heteroalkynylene, arylene, heteroarylene, —C(O)$R^M$—, —C(O)O$R^M$—, wherein $R^M$ is selected from the group consisting of $C_{1-10}$ alkylene, $C_{2-10}$ alkenylene and $C_{2-10}$ alkynylene, and wherein the alkylene, alkenylene, alkynylene, cycloalkylene, cycloalkenylene, heteroalkylene, heteroalkenylene, heteroalkynylene, arylene and heteroarylene groups may be optionally substituted with one or more $R^N$, wherein each $R^N$ is independently selected from the group consisting of —H, —OH, —CN, —NO$_2$, —CF$_3$, —OCF$_3$, —CO$_2$H, —NH$_2$, $C_1$-$C_{10}$ alkyl, $C_2$-$C_{10}$ alkenyl, $C_2$-$C_{10}$ alkynyl, —O($C_1$-$C_{10}$ alkyl), —O($C_2$-$C_{10}$ alkenyl), —O($C_2$-$C_{10}$ alkynyl), halogen, —C(O)H, —C(O)—($C_1$-$C_{10}$ alkyl), —C(O)—O($C_1$-$C_{10}$ alkyl), —NH($C_1$-$C_{10}$ alkyl), —N($C_1$-$C_{10}$ alkyl)$_2$, —C(O)—NH($C_1$-$C_{10}$ alkyl), —C(O)—N($C_1$-$C_{10}$ alkyl)$_2$, —NH—C(O)—($C_1$-$C_{10}$ alkyl), —NH($C_1$-$C_{10}$ alkyl)-C(O)—($C_1$-$C_{10}$ alkyl), —NH—S(O)$_2$—($C_1$-$C_{10}$ alkyl), —NH—($C_1$-$C_{10}$ alkyl)-S(O)$_2$—($C_1$-$C_{10}$ alkyl), —($C_0$-$C_{10}$)—SH, —S(O)—($C_1$-$C_{10}$ alkyl), —S(O)$_2$—($C_1$-$C_{10}$ alkyl), —S(O)$_2$—NH$_2$, —S(O)$_2$—NH—($C_1$-$C_{10}$ alkyl), —S(O)$_2$—N($C_1$-$C_{10}$ alkyl)$_2$ and =O, and d is an integer from 1 to 4, wherein if Z is directly bonded to an O or N atom, z is 0 and otherwise z is 1;

group (IIE) has the formula:

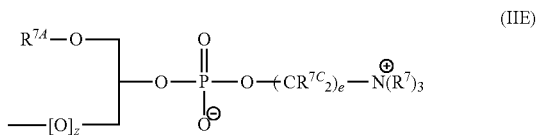

(IIE)

wherein each $R^7$ and $R^{7C}$ is independently selected from hydrogen and $C_{1-4}$ alkyl; $R^{7A}$ is hydrogen or a group —C(O)B$^2R^{7B}$, wherein $R^{7B}$ is hydrogen or methyl, B$^2$ is selected from the group consisting of a bond; $C_{1-10}$ alkylene, $C_{2-10}$ alkenylene, $C_{2-10}$ alkynylene, $C_{3-10}$ cycloalkylene, $C_{3-10}$ cycloalkenylene, heteroalkylene, $C_{2-10}$ heteroalkenylene, $C_{2-10}$ heteroalkynylene, arylene, heteroarylene, —C(O)$R^M$—, —C(O)O$R^M$—, wherein $R^M$ is selected from the group consisting of $C_{1-10}$ alkylene, $C_{2-10}$ alkenylene and $C_{2-10}$ alkynylene, and wherein the alkylene, alkenylene, alkynylene, cycloalkylene, cycloalkenylene, heteroalkylene, heteroalkenylene, heteroalkynylene, arylene and heteroarylene groups may be optionally substituted with one or more $R^N$, wherein each $R^N$ is independently selected from the group consisting of —H, —OH, —CN, —NO$_2$, —CF$_3$, —OCF$_3$, —CO$_2$H, —NH$_2$, $C_1$-$C_{10}$ alkyl, $C_2$-$C_{10}$ alkenyl, $C_2$-$C_{10}$ alkynyl, —O($C_1$-$C_{10}$ alkyl), —O($C_2$-$C_{10}$ alkenyl), —O($C_2$-$C_{10}$ alkynyl), halogen, —C(O)H, —C(O)—($C_1$-$C_{10}$ alkyl), —C(O)—O($C_1$-$C_{10}$ alkyl), —NH($C_1$-$C_{10}$ alkyl), —N($C_1$-$C_{10}$ alkyl)$_2$, —C(O)—NH($C_1$-$C_{10}$ alkyl), —C(O)—N($C_1$-$C_{10}$ alkyl)$_2$, —NH—C(O)—($C_1$-$C_{10}$ alkyl), —NH($C_1$-$C_{10}$ alkyl)-C(O)—($C_1$-$C_{10}$ alkyl), —NH—S(O)$_2$—($C_1$-$C_{10}$ alkyl), —NH—($C_1$-$C_{10}$ alkyl)-S(O)$_2$—($C_1$-$C_{10}$ alkyl), —($C_0$-$C_{10}$)—SH, —S(O)—($C_1$-$C_{10}$ alkyl), —S(O)$_2$—($C_1$-$C_{10}$ alkyl), —S(O)$_2$—NH$_2$, —S(O)$_2$—NH—($C_1$-$C_{10}$ alkyl), —S(O)$_2$—N($C_1$-$C_{10}$ alkyl)$_2$ and =O, and e is an integer from 1 to 4, wherein if Z is directly bonded to an O or N atom, z is 0 and otherwise z is 1;

14. A monomer according to any preceding clause, wherein Z is a group (JIB).

15. A monomer according to clause 14, wherein $R^4$ is methyl and b is 2.

16. A monomer according to any preceding clause, wherein n is 0 or 1.

17. A monomer according to clause 16, wherein n is 0.

18. A monomer according to clause 1, wherein n is 0; X is NR$^2$; Y, R$^2$ and the N atom to which they are bonded together form a 5-membered heterocyclic ring substituted with =O; x is 2; and Z is a group of formula (IIB), wherein each $R^4$ is methyl and b is 2.

19. A monomer according to clause 1 of formula (IB):

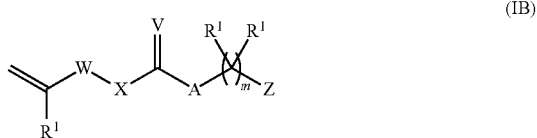

(IB)

wherein W, X and Z, $R^1$, $R^2$, n and m are as defined in connection with formula (I) in clause 1, V is S or O; and A is selected from NR$^M$, O and S, wherein $R^M$ is hydrogen or $C_{1-4}$ alkyl.

20. A monomer according to clause 1 of formula (IC):

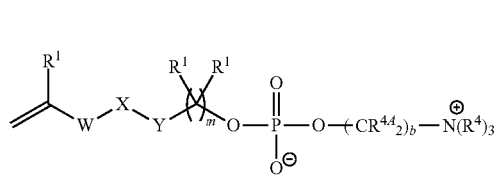

wherein W, X, Y, $R^1$, $R^2$, m and n are as defined in clause 1, each $R^4$ and $R^{4A}$ is independently selected from hydrogen and $C_{1-4}$ alkyl and b is an integer from 1 to 4.

21. A monomer according to clause of formula (ID):

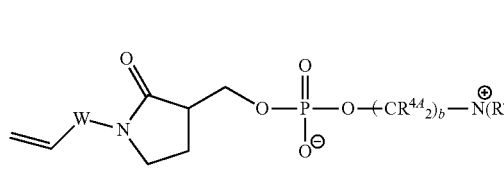

wherein W is as defined in connection with formula (I), each $R^4$ and $R^{4A}$ is independently selected from hydrogen and $C_{1-4}$ alkyl and b is an integer from 1 to 4.

22. A monomer according to clause 1, which has formula (IE):

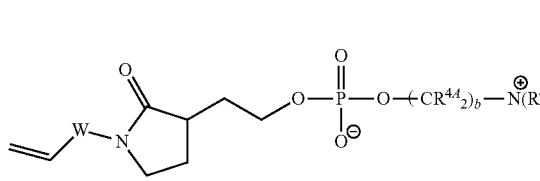

wherein W is as defined in connection with formula (I), each $R^4$ and $R^{4A}$ is independently selected from hydrogen and $C_{1-4}$ alkyl and b is an integer from 1 to 4.

23. A polymer obtainable by reacting a monomer as defined in any preceding clause with a co-monomer system.

24. A polymer according to clause 23, wherein the co-monomer system comprises a siloxane group-containing monomer or macromer.

25. A polymer according to clause 24, wherein the siloxane group-containing monomer is a material of formula (A) or (B):

$$(T^1-Y^1)_k-G^1(Y^2-Z)_l \quad (A)$$

$$[(T^1)_k-Y^3(Z)_u]_v-G^1-R^{24} \quad (B)$$

wherein
$T^1$ is a polymerisable group;
$Y^1$ and $Y^2$ are each independently a linker group selected from the group consisting of a bond, $C_{1-12}$ alkylene, $C_{2-12}$ alkenylene, $C_{2-12}$ alkynylene, $C_{3-12}$ cycloalkylene, $C_{3-12}$ cycloalkenylene, $C_{2-12}$ heteroalkenylene, $C_{2-12}$ heteroalkynylene, arylene, heteroarylene, —C(O)—$C_{1-12}$ alkylene, —C(S)—$C_{1-12}$ alkylene, —C(O)O—$C_{1-12}$ alkylene, —C(O)S—$C_{1-12}$ alkylene, —C(O)N($R^{1''}$)—$C_{1-12}$ alkylene, —C(S)—$C_{1-12}$ alkylene, —C(S)O—$C_{1-12}$ alkylene, —C(S)S—$C_{1-12}$ alkylene, —C(S)N($R^{M}$)—$C_{1-12}$ alkylene, —$(CH_2)_{qq}$(OCH$_2$CH$_2$)$_{rr}$— and —$(CH_2CH_2O)_{rr}(CH_2)_{qq}$—, wherein $R^M$ is hydrogen or $C_{1-4}$ alkyl, qq is an integer from 1 to 10, rr is an integer from 1 to 10, wherein one or more carbon atoms in the $C_{1-12}$ alkylene group may be optionally replaced with a heteroatom selected from the group consisting of S and O and the alkylene, alkenylene, alkynylene, cycloalkylene, cycloalkenylene, heteroalkenylene, heteroalkynylene, arylene and heteroarylene groups may be optionally substituted with one or more $R^N$, wherein each $R^N$ is independently selected from the group consisting of —H, —OH, —CN, —NO$_2$, —CF$_3$, —OCF$_3$, —CO$_2$H, —NH$_2$, $C_1$-$C_{10}$ alkyl, $C_2$-$C_{10}$ alkenyl, $C_2$-$C_{10}$ alkynyl, —O($C_1$-$C_{10}$ alkyl), —O($C_2$-$C_{10}$ alkenyl), —O($C_2$-$C_{10}$ alkynyl), halogen, —C(O)H, —C(O)—($C_1$-$C_{10}$ alkyl), —C(O)—O($C_1$-$C_{10}$ alkyl), —NH($C_1$-$C_{10}$ alkyl), —N($C_1$-$C_{10}$ alkyl)$_2$, —C(O)—NH($C_1$-$C_{10}$ alkyl), —C(O)—N($C_1$-$C_{10}$ alkyl)$_2$, —NH—C(O)—($C_1$-$C_{10}$ alkyl), —NH($C_1$-$C_{10}$ alkyl)-C(O)—($C_1$-$C_{10}$ alkyl), —NH—S(O)$_2$—($C_1$-$C_{10}$ alkyl), —NH—($C_1$-$C_{10}$ alkyl)-S(O)$_2$—($C_1$-$C_{10}$ alkyl), —($C_0$-$C_{10}$)—SH, —S(O)—($C_1$-$C_{10}$ alkyl), —S(O)$_2$—($C_1$-$C_{10}$ alkyl), —S(O)$_2$—NH$_2$, —S(O)$_2$—NH—($C_1$-$C_{10}$ alkyl), —S(O)$_2$—N($C_1$-$C_{10}$ alkyl)$_2$ and =O;
$Y^3$ is a linker group;
$R^{24}$ is a $C_{1-12}$ alkyl group which may be optionally substituted with one or more $R^N$;
$G^1$ is a siloxane group-containing component;
Z is a zwitterionic group;
k is an integer from 1 to 10;
l is an integer from 1 to 3;
u is an integer from 1 to 3; and
v is an integer from 1 to 3.

26. A polymer according to clause 24 or clause 25, wherein the co-monomer system comprises a monomer comprising a vinyl group.

27. A polymer according to any one of clauses 24 to 26, which has an oxygen permeability of about 30 barriers or more.

28. A polymer according to any one of clauses 24 to 27, which has an equilibrium water content in the range from 30 to 50%.

29. A polymer according to any one of clauses 24 to 28, which has a modulus of less than 3 MPa.

30. An article comprising a polymer as defined in any one of clauses 24 to 29.

31. An article according to clause 30, which is an ophthalmic lens.

32. An article according to clause 31, which is a contact lens.

33. An article comprising a surface having coated thereon a polymer as defined in any one of clauses 24 to 29.

34. An article according to clause 33, which is a contact lens.

35. A method of coating an article having a surface comprising applying a polymer as defined in any one of clauses 24 to 29 to the surface of the article.

Measurement Methods

Tensile Modulus

The Young's modulus of the lens materials were determined using a TA-XT2 Texture Analyser, and the value was obtained by drawing a tangent to the initial linear portion of the stress-strain curve, and dividing the tensile stress by the corresponding strain. Measurements were performed on films of 500 μm thickness prepared from the formulations and cut into 10 mm×50 mm samples.

Equilibrium Water Content

The Equilibrium Water Contents (EWC) of the prototype hydrogel lenses produced according to the present invention were determined by gravimetric means. The wet weight of lenses after equilibration in water at room temperature overnight was first measured. The lenses were then dried in an oven at 70° C. to a constant weight, which was the dry weight. The EWC of the lenses was then calculated as follows.

EWC(wt %)=[(wet weight−dry weight)/wet weight]*100

Oxygen Permeability

The oxygen permeability (in barriers) of prototype lenses produced according to the method of the present invention was determined by the polargraphic method generally described in ISO 9913-1:1996(E).

MODES FOR CARRYING OUT THE INVENTION

The following examples describe the syntheses of monomers of formula (I). These examples are intended to illustrate the invention and are not to be construed as being limitations thereon.

Example 1

Preparation of 2-(3-oxyethyl-1-vinylpyrrolidin-2-one)-2'-(trimethylammonium)-ethyl phosphate, inner salt (HEVP-PC)

The reactions carried out in Example 1 are summarised in scheme 1 below:

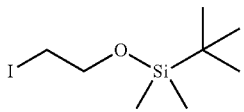

$C_8H_{19}IOSi$ (M = 286.23 g/mol)

$^1$H-NMR (400 MHz) (CDCl$_3$): δ=3.83 (t, 2H, J=7.0 Hz), 3.83 (t, 2H, J=7.0 Hz), 3.20 (t, 2H, J=7 Hz), 0.90 (s, 9H), 0.08 (s, 6H) ppm.

ii) Preparation of 3-[2-(tert-butyldimethylsilanyloxy)-ethyl]-1-vinylpyrrolidin-2-one (TBSE-VP To a stirred ice-cold solution of diisopropylamine (0.46 mL; 3.3 mmol; 1.1 equiv.) in dry tetrahydrofuran (20 mL) was dropwise added a 2.5 m solution of n-butyllithium (1.32 mL; 3.3 mmol; 1.1 equiv.) under an argon atmosphere. Upon complete addition the solution was left stirring for 10 min and then

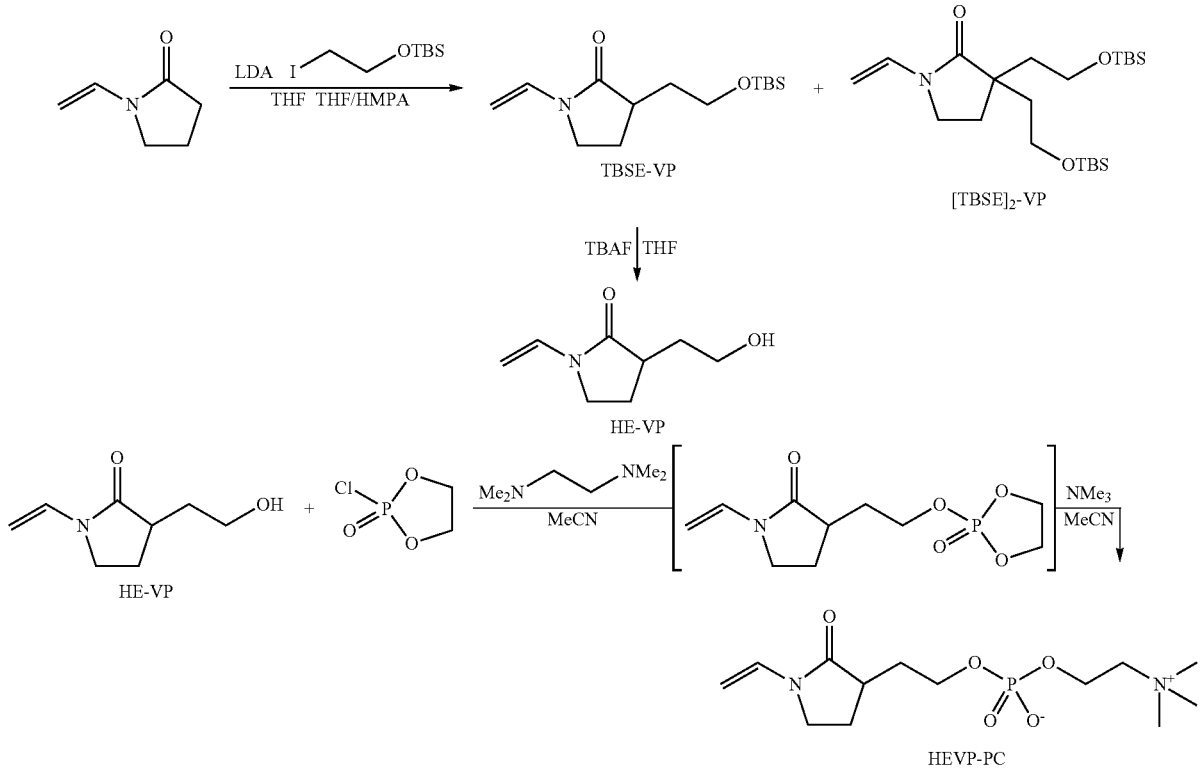

(i) Preparation of (2-iodoethoxy)-tert-butyldimethylsilane

To a stirred solution of 2-iodoethanol (17.2 g; 100 mmol) and imidazole (8.17 g; 120 mmol) in dichloromethane (100 mL) was added tert-butyldimethylsilyl chloride (15.83 g; 105 mmol) at such a rate that the reaction temperature did not rise above 30° C. Upon complete addition the solution was left stirring for 17 h, then washed with water (2×50 mL) and brine (50 mL) and dried over MgSO$_4$. Evaporation of the solvent afforded the target compound (28.0 g; 97.8 mmol; 98%) as a colourless liquid.

cooled to around −80 to −70° C. 1-vinylpyrrolidin-2-one (0.32 mL; 3.0 mmol) was added dropwise and the solution was left stirring for 20 min. Hexamethylphosphoramide (0.57 mL; 3.3 mmol; 1.1 equiv.) was added and the solution left stirring for further 20 min. To the solution was dropwise added (2-iodoethoxy)-tert-butyldimethylsilane (859 mg; 3.0 mmol) and the solution was left stirring at around −80 to −70° C. for 17 h. The reaction mixture was warmed to ambient temperature and quenched with a saturated aqueous solution of NH$_4$Cl (15 mL). The aqueous phase was extracted with diethyl ether (2×15 mL), the combined organic extracts were dried over MgSO$_4$ and concentrated under reduced pressure. Column chromatography (ethyl acetate/petroleum ether (b.p.

40-60° C.)=1:9) afforded by-product 3,3-bis-[2-(tert-butyldimethylsilanyloxy)-ethyl]-1-vinylpyrrolidin-2-one ([TBSE] 2-VP) (49 mg; 0.115 mmol; 4%) as a colourless liquid. Further elution with ethyl acetate/petroleum ether (b.p. 40-60° C.) (1:4) afforded the target compound 3-[2-(tert-butyldimethylsilanyloxy)-ethyl]-1-vinylpyrrolidin-2-one (TBSE-VP) (621 mg; 2.30 mmol; 77%) as a colourless liquid.

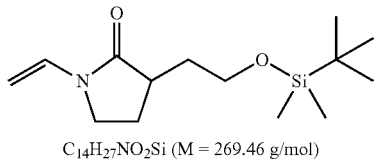 [SMILES: C=CN1CCC(CCO[Si](C)(C)C(C)(C)C)C1=O]

$C_{14}H_{27}NO_2Si$ (M = 269.46 g/mol)

$^1$H-NMR (400 MHz) (CD$_3$OD): δ=7.01 (dd, 1H, —CH=CH$_2$, $J_{cis}$=9.1 Hz, $J_{trans}$=16.0 Hz), 4.53 (d, 1H, =CH$_2$, $J_{trans}$=16.0 Hz), 4.49 (d, 1H, =CH$_2$, $J_{cis}$=9.1 Hz), 3.83-3.70 (m, 2H, —CH$_2$O—), 3.57 (td, 1H, —CH$_2$N—, J=9.9 Hz, 3.0 Hz), 3.48-3.40 (m, 1H, —CH$_2$N—), 2.76-2.65 (m, 1H, —CH—(C=O)—), 2.39-2.28 and 1.90-1.79 (2×m, 2H, —CH$_2$—CH$_2$N—), 2.10-2.00 and 1.63-1.52 (2×m, 2H, —CH$_2$—CH$_2$O—), 0.90 (s, 9H, —C(CH$_3$)$_3$), 0.07 (s, 6H, —Si(CH$_3$)$_2$—) ppm.

iii) Preparation of 3-(2-hydroxyethyl)-1-vinylpyrrolidin-2-one (HE-VP

To a stirred and ice-cold solution of 3-[2-(tert-butyldimethylsilanyloxy)-ethyl]-1-vinylpyrrolidin-2-one (TBSE-VP) (269 mg; 1.0 mmol) in dry tetrahydrofuran (10 mL) was dropwise added a 1.0 m solution of tetrabutylammonium fluoride (2.0 mL; 2.0 mmol; 2.0 equiv.) under an argon atmosphere. Upon completion of the addition the reaction mixture was left stirring at 0° C. for 5 min, allowed to warm to ambient temperature over 5 min and left stirring for another 40 min. The reaction mixture was partitioned between water (5 mL) and ethyl acetate (10 mL) and the aqueous phase was extracted with ethyl acetate (3×5 mL). The combined organic extracts were dried over MgSO$_4$ and concentrated under reduced pressure. Column chromatography (ethyl acetate) afforded the target compound (135 mg; 0.87 mmol; 87%) as a pale yellow liquid.

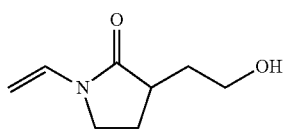

$C_8H_{13}NO_2$ (M = 155.19 g/mol)

$^1$H-NMR (400 MHz) (CD$_3$OD): δ=7.02 (dd, 1H, —CH=CH$_2$, $J_{cis}$=9.1 Hz, $J_{trans}$=16.0 Hz), 4.54 (d, 1H, =CH$_2$, $J_{trans}$=16.0 Hz), 4.50 (d, 1H, =CH$_2$, $J_{cis}$=9.1 Hz), 3.75-3.62 (m, 2H, —CH$_2$O—), 3.59 (td, 1H, J=9.8 Hz, 3.0 Hz), 3.44 (dt, 1H, J=10.2 Hz, 8.2 Hz), 2.70 (qd, 1H, —CH—(C=O)—, J=9.1 Hz, 5.0 Hz), 2.36 (dddd, 1H, —CH$_2$—CH$_2$N—, J=15.7 Hz, 8.8 Hz, 7.9 Hz, 2.9 Hz), 2.06 (dddd, 1H, —CH$_2$—CH$_2$O—, J=19.1 Hz, 7.8 Hz, 6.6 Hz, 5.0 Hz), 1.80 (ddd, 1H, —CH$_2$—CH$_2$N—, J=17.8 Hz, 12.8 Hz, 9.2 Hz), 1.56 (ddt, 1H, —CH$_2$—CH$_2$O—, J=13.8 Hz, 9.2 Hz, 5.7 Hz) ppm.

iv) Preparation of 2-(3-oxyethyl-1-vinylpyrrolidin-2-one)-2'-(trimethylammonium)-ethyl phosphate, inner salt (HEVP-PC To a stirred and chilled (−10° C.) solution of 2-chloro-2-oxo-1,3,2-dioxaphospholane (4.58 g; 32.1 mmol; 1.04 equiv.) in acetonitrile (3 g) was dropwise added a solution of 3-(2-hydroxyethyl)-1-vinylpyrrolidin-2-one (4.80 g; 30.9 mmol) and N,N,N',N'-tetramethylethylenediamine (1.98 g; 17.1 mmol; 0.55 equiv.) in acetonitrile (7 g). Upon completion of the addition the reaction mixture was left stirring for 15 min, filtered under an argon atmosphere and the N,N,N',N'-tetramethylethylenediaminedihydrochloride precipitate washed with dry acetonitrile (7 g) to give a filtrate comprising a solution of 2-(3-oxyethyl-1-vinylpyrrolidin-2-one)-2-oxo-1,3,2-dioxaphospholane in acetonitrile.

To the stirred and chilled phospholane solution was added 4-methoxyphenol (4 mg; 0.029 mmol), acetonitrile (30 g) and trimethylamine (3.7 g; 62.6 mmol; 2.02 equiv.) and the reaction mixture was heated in a closed system (water condenser fitted with balloon) at 70° C. for 19 h. The reaction mixture was concentrated (ca. 10 to 20 mL of acetonitrile and excess trimethylamine removed) under vacuum and the product allowed to crystallise out of solution at 5° C. and allowed to warm to ambient temperature. The crystalline product was filtered under argon atmosphere, successively washed with acetonitrile (6 mL) and ethyl acetate (3×6 mL) and dried in vacuo at ambient temperature to afford 2.95 g of a white powder comprising the target compound (2.83 g; 8.83 mmol; 29%) and residual acetonitrile (0.12 g; 2.94 mmol).

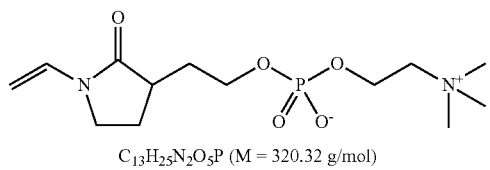 [SMILES: C=CN1CCC(CCOP(=O)([O-])OCC[N+](C)(C)C)C1=O]

$C_{13}H_{25}N_2O_5P$ (M = 320.32 g/mol)

$^1$H-NMR (400 MHz) (CD$_3$OD): δ=7.01 (dd, 1H, —CH=CH$_2$, $J_{cis}$=9.1 Hz, $J_{trans}$=16.0 Hz), 4.54 (d, 1H, =CH$_2$, $J_{trans}$=16.0 Hz), 4.49 (d, 1H, =CH$_2$, $J_{cis}$=9.1 Hz), 4.31-4.23 (m, 2H, —OCH$_2$—CH$_2$N$^+$—), 4.10-3.93 (m, 2H, —CH—CH$_2$—CH$_2$O—), 3.67-3.62 (m, 2H, —CH$_2$N$^+$—), 3.62-3.55 and 3.49-3.40 (2×m, 2H, —CH$_2$N—), 3.23 (s, 9H, —N$^+$(CH$_3$)$_3$), 2.81-2.72 (m, 1H, —CH—(C=O)—), 2.39-2.28 and 1.90-1.79 (2×m, 2H, —CH$_2$—CH$_2$N—), 2.10-2.00 and 1.63-1.52 (2×m, 2H, —CH—CH$_2$—CH$_2$O—) ppm. $^{13}$C-NMR (100 MHz) (CD$_3$OD): δ=176.39 (—(C=O)—), 129.38 (—CH=CH$_2$), 95.00 (=CH$_2$), 66.69 (—CH$_2$N$^+$—), 63.86 and 63.80 (—CH—CH$_2$—CH$_2$O—), 59.56 and 59.51 (–OCH$_2$—CH$_2$N$^+$—), 53.91, 53.87 and 53.81 (—N$^+$(CH$_3$)$_3$), 43.47 (—CH$_2$N—), 39.90 (—CH—(C=O)—), 32.51 and 32.42 (—CH—CH$_2$—CH$_2$O—), 24.82 (—CH$_2$—CH$_2$N—) ppm. $^{31}$P-NMR (162 MHz) (CD$_3$OD): δ=−0.14 ppm. HRMS (ESI) for $C_{13}H_{26}N_2O_5P$ [M+H]$^+$: calculated: 321.1574

Example 2

Preparation of 2-(trimethylammonium)ethyl-2-(vinyloxycarbonylamino)ethyl phosphate, inner salt (HEVC-PC)

The reactions carried out in Example 2 are summarised in scheme 2 below:

Scheme 2

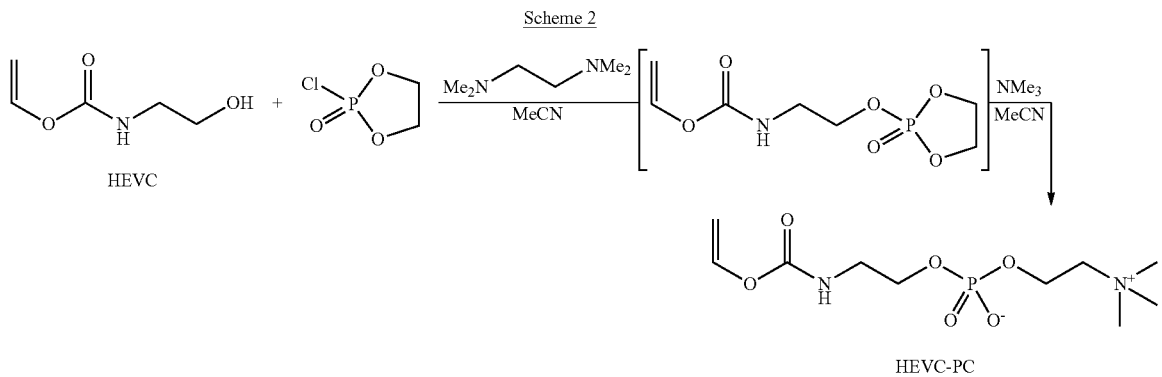

To a stirred and chilled (−10° C.) solution of 2-chloro-2-oxo-1,3,2-dioxaphospholane (5.00 g; 35.1 mmol) in acetonitrile (3 g) was dropwise added a solution of N-hydroxyethyl-O-vinylcarbamate (HEVC) (4.60 g; 35.1 mmol) and N,N,N',N'-tetramethylethylenediamine (2.24 g; 19.3 mmol; 0.55 equiv.) in acetonitrile (7.5 g). Upon completion of the addition the reaction mixture was left stirring for 1 h, filtered under an argon atmosphere and the N,N,N',N'-tetramethylethylenediamine dihydrochloride precipitate washed with dry acetonitrile (8 g) to give a filtrate comprising a solution of 2-(N-oxyethyl-O-vinylcarbamate)-2-oxo-1,3,2-dioxaphospholane in acetonitrile.

To the stirred and chilled phospholane solution was added 4-methoxyphenol (20 mg; 0.161 mmol), acetonitrile (35 g) and trimethylamine (3.67 g; 61.4 mmol; 1.75 equiv.) and the reaction mixture was heated in a closed system (water condenser fitted with balloon) at 70° C. for 17 h. The reaction mixture was concentrated (ca. 10 mL of acetonitrile and excess trimethylamine removed) under vacuum and the product allowed to crystallise out of solution at around −25° C.

The crystalline product was rapidly filtered and dried in vacuo at ambient temperature to afford the target compound (1.08 g; 3.65 mmol; 10%) as an off-white solid.

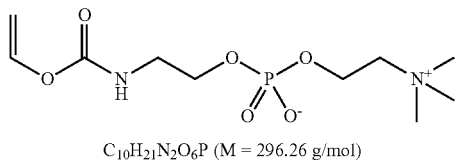 [SMILES: C=COC(=O)NCCOP(=O)([O-])OCC[N+](C)(C)C]

$C_{10}H_{21}N_2O_6P$ (M = 296.26 g/mol)

$^1$H-NMR (400 MHz) (CD$_3$OD): δ=7.16 (dd, 1H, —CH=CH$_2$, J$_{cis}$=6.3 Hz, J$_{trans}$=14.0 Hz), 4.71 (dd, 1H, =CH$_2$, J$_{gem}$=1.4 Hz, J$_{trans}$=14.0 Hz), 4.41 (dd, 1H, =CH$_2$, J$_{gem}$=1.4 Hz, J$_{cis}$=6.3 Hz), 4.32-4.23 (m, 2H, —OCH$_2$—CH$_2$N$^+$—), 3.93 and 3.91 (2×t, 2H, —NH—CH$_2$—CH$_2$O—, J=5.5 Hz), 3.68-3.60 (m, 2H, —CH$_2$N$^+$—), 3.37 (t, 2H, —NH—CH$_2$—, J=5.5 Hz), 3.22 (s, 9H, —N$^+$(CH$_3$)$_3$) ppm. $^{31}$P-NMR (162 MHz) (CD$_3$OD): δ=−0.12 ppm.

Example 3

Preparation of 2-(trimethylammonium)ethyl-2-(vinylaminocarbonyloxy)ethyl phosphate, inner salt (VAC-PC)

The reaction carried out in Example 3 is summarised in Scheme 3 below:

Scheme 3

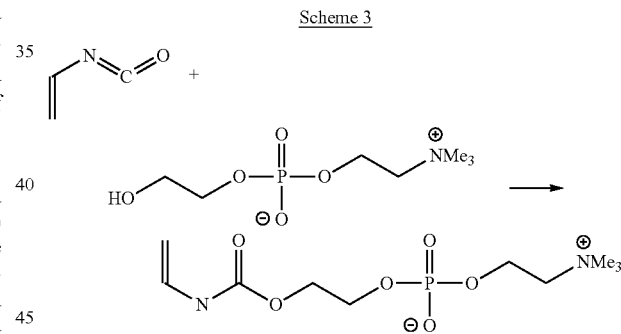

Hydroxyethylphosphorylcholine (0.11 g, 0.4 mmol) as a suspension in dimethylsulphoxide (1.2 g) with tris(2-(2-methoxyethoxy)ethyl)amine (0.04 g, 0.1 mmol) was stirred under a nitrogen atmosphere while vinylisocyanate (0.04 g, 0.6 mmol) was added portion wise over 15 minutes. The mixture was stirred at room temperature for 3 days and then the solution was added to MEK (30 g) under nitrogen and stirred for 30 minutes. The white solid that separated was collected by filtration, washed with MEK and dried under vacuum (0.09 g, 0.3 mmol, 63%).
$^1$H-NMR (400 MHz) (d$^6$DMSO): δ=6.55 (1H, m), 4.52 (1H, d), 4.15 (1H, d), 4.10 (2H, m), 4.02 (2H, m), 3.78 (2H, m), 3.52 (2H, m) and 3.15 (9H, s) ppm, $^{13}$C-NMR (100 MHz) (d$^6$DMSO): δ=157.2, 130.9, 92.9, 65.5, 62.3, 62.3, 58.2 and 53.1 ppm, $^{31}$P-NMR (162 MHz) (d$^6$DMSO): δ=−0.12 ppm.

Example 4

Polymer Systems were Made Using the Following General Procedure

Monomer components indicated in table 1 were mixed, degassed using argon and heated to 70° C. for 1 hr. to give the cross-linked polymer systems derived from the monomer feedstocks.

TABLE 1

| Formulation | NVP-PC | HEVC-PC | HEMA | VP | DMA | SC1 | SC6 | EGDMA | PD16 |
|---|---|---|---|---|---|---|---|---|---|
| LN007/2/201 | 14.74 | 0 | 49.14 | 0 | 0 | 0 | 34.40 | 0.74 | 0.98 |
| LN007/2/202 | 19.66 | 0 | 44.23 | 0 | 0 | 0 | 34.40 | 0.74 | 0.98 |
| LN007/2/203 | 9.83 | 0 | 58.97 | 0 | 0 | 0 | 29.48 | 0.74 | 0.98 |
| LN007/2/204 | 4.91 | 0 | 63.88 | 0 | 0 | 0 | 29.48 | 0.74 | 0.98 |
| LN007/2/205 | 9.83 | 0 | 68.8 | 0 | 0 | 0 | 19.66 | 0.74 | 0.98 |
| LN007/2/206 | 4.91 | 0 | 73.71 | 0 | 0 | 0 | 19.66 | 0.74 | 0.98 |
| LN007/2/292 | 14.74 | 0 | 24.57 | 18.67 | 10.81 | 29.48 | 0 | 0.74 | 0.98 |
| LN007/2/207 | 9.83 | 0 | 88.45 | 0 | 0 | 0 | 0 | 0.74 | 0.98 |
| LN007/2/208 | 19.66 | 0 | 78.62 | 0 | 0 | 0 | 0 | 0.74 | 0.98 |
| LN007/2/213 | 15.71 | 0 | 83.05 | 0 | 0 | 0 | 0 | 0.75 | 0.49 |
| LN007/2/369 | 15.71 | 0 | 83.05 | 0 | 0 | 0 | 0 | 0.75 | 0.49 |
| LN007/2/354 | 9.83 | 0 | 58.97 | 0 | 0 | 29.48 | 0 | 0.74 | 0.98 |
| LN007/2/355 | 19.66 | 0 | 49.14 | 0 | 0 | 29.48 | 0 | 0.74 | 0.98 |
| LN007/2/214 | 8.85 | 0 | 24.57 | 24.57 | 10.81 | 29.48 | 0 | 0.74 | 0.98 |
| LN007/2/215 | 7.85 | 0 | 90.91 | 0 | 0 | 0 | 0 | 0.75 | 0.49 |
| LN007/2/370 | 8.85 | 0 | 24.57 | 24.57 | 10.81 | 29.48 | 0 | 0.74 | 0.98 |
| LN007/2/393 | 0 | 7.37 | 90.91 | 0.00 | 0.00 | 0.00 | 0.00 | 0.74 | 0.98 |

Example 5

This example describes the general procedure for preparing polymerisable materials and corresponding contact lenses (Table 2). Unless otherwise stated, all the materials were used as received.

Each component of the polymerisable system including the monomers, cross linker (EGDMA) and initiator (PD16) was weighed and added to a glass vial. The vials were sealed with a cap and then placed on a roller mixer at room temperature until all components were fully dissolved. After dissolution, the mixture was filtered through a 0.45 micron filter and the solution was de-oxygenated by gently bubbling dry argon gas through the formulation.

Polypropylene contact lens molds were cleaned by rinsing with 20% Decon 90 in water followed by drying in an oven at 70° C. for 30 min. The female molds were filled with the formulation and the male molds were added to the female molds. The molds were then placed in an oven preheated to 70° C. for 1 hour.

After cooling, the molds were immersed in purified water overnight to de-mold the lenses.

TABLE 2

| Description | Procedure |
|---|---|
| 1. Mixing | weigh components used to form the polymerisable solution into a glass vial |
| | seal the vial with a lid |
| | place on a roller-mixer at room temperature until fully dissolved, filter through 0.45 micron membrane and de-oxygenate |
| 2. Preparation and filling the molds | rinse the plastic molds with 20% Decon 90 in water |
| | dry the molds in an oven at 70° C. for 30 min |
| | fill the molds with the polymerisable solution and close |
| 3. Polymerization | preheat the oven to 70° C. |
| | place the material-containing molds in the oven for 1 hr and then allow to cool for 30 mins |
| 4. Hydration and Demolding | place the lenses/molds in purified water |
| | open the molds and leave overnight |
| | remove the lenses from the molds |

Example 6

The monomers were mixed with other components as listed in table 3 below and used to form contact lenses according to the methodology set out in table 2. The abbreviations and corresponding full names of the components are listed in Table 4.

TABLE 3

| Formulation | NVP-PC | HEVC-PC | HEMA | VP | DMA | SC1 | EGDMA | PD16 | Hydrogel appearance | Water content (%) |
|---|---|---|---|---|---|---|---|---|---|---|
| LN007/2/207 | 9.83 | 0 | 88.45 | 0 | 0 | 0 | 0.74 | 0.98 | clear | nd |
| LN007/2/208 | 19.66 | 0 | 78.62 | 0 | 0 | 0 | 0.74 | 0.98 | clear | nd |
| LN007/2/213 | 15.71 | 0 | 83.05 | 0 | 0 | 0 | 0.75 | 0.49 | clear | 58.3 |
| LN007/2/354 | 9.83 | 0 | 58.97 | 0 | 0 | 29.48 | 0.74 | 0.98 | clear | 32.6 |
| LN007/2/355 | 19.66 | 0 | 49.14 | 0 | 0 | 29.48 | 0.74 | 0.98 | clear | 42.6 |
| LN007/2/214 | 8.85 | 0 | 24.57 | 24.57 | 10.81 | 29.48 | 0.74 | 0.98 | clear | 38.5 |
| LN007/2/215 | 7.85 | 0 | 90.91 | 0 | 0 | 0 | 0.75 | 0.49 | clear | 47.7 |
| LN007/2/370 | 8.85 | 0 | 24.57 | 24.57 | 10.81 | 29.48 | 0.74 | 0.98 | clear | 40.9 |
| LN007/2/393 | 0 | 7.37 | 90.91 | 0 | 0 | 0 | 0.74 | 0.98 | slightly hazy | 37.0 |

TABLE 4

| Abbreviation | Full name |
|---|---|
| NVP-PC | 2-(3-Oxyethyl-1-vinylpyrrolidin-2-one)-2'-(trimethylammonium)-ethyl phosphate, inner salt |
| HEVC-PC | 2-(Trimethylammonium)ethyl-2-(vinyloxycarbonylamino)ethyl phosphate, inner salt |
| HEMA | 2-Hydroxyethylmethacrylate |
| VP | N-Vinylpyrrolidone |
| DMA | Dimethylacrylamide |
| SC1 | (3-Methacryloxy-2-hydroxypropoxy)-propylbis(trimethylsiloxy)-methylsilane |
| SC6 | Poly(dimethylsiloxane), monomethacryloxypropyl substituted, di-hydroxypropyl terminated |
| EGDMA | Ethyleneglycoldimethacrylate |
| PD16 | Bis(tert-butylcyclohexyl) peroxydicarbonate |

Example 7

The equilibrium water content (EWC) of certain of the prototype lenses was determined by gravimetric means. The wet weight of the lens after equilibration in water at room temperature overnight was first measured. The lens was then dried in an oven at 70° C. to a constant weight, which was the dry weight. The water content of the lenses was calculated as follows.

EWC(wt %)=[(wet weight−dry weight)/wet weight]*100

The EWC of certain of the polymers of example 6 are shown in table 3.

What is claimed is:

1. A monomer of formula (I):

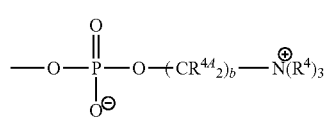

(I)

wherein:
W is $(CR^1_2)_n$;
Z is a zwitterionic group selected from the group consisting of (IIA), (IIB), (IIC), (IID) and (IIE), wherein group (IIA) has the formula:

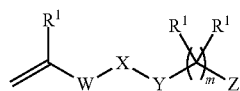

(IIA)

wherein each $R^3$ and $R^{3A}$ is independently selected from hydrogen and $C_{1-4}$ alkyl and a is an integer from 2 to 4;
group (IIB) has the formula:

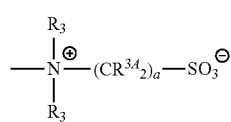

(IIB)

wherein each $R^4$ and $R^{4A}$ is independently selected from hydrogen and $C_{1-4}$ alkyl and b is an integer from 1 to 4;

group (IIC) has the formula:

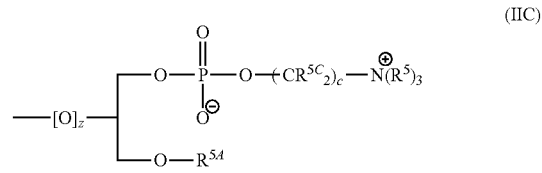

(IIC)

wherein each $R^5$ and $R^{5C}$ is independently selected from hydrogen and $C_{1-4}$ alkyl; $R^{5A}$ is hydrogen or a group —C(O)B$^1$R$^{5B}$, wherein R$^{5B}$ is hydrogen or methyl, B$^1$ is selected from the group consisting of a bond; $C_{1-10}$ alkylene, $C_{2-10}$ alkenylene, $C_{2-10}$ alkynylene, $C_{3-10}$ cycloalkylene, $C_{3-10}$ cycloalkenylene, $C_{1-10}$ heteroalkylene, $C_{2-10}$ heteroalkenylene, $C_{2-10}$ heteroalkynylene, arylene, heteroarylene, —C(O)R$^M$—, —C(O)OR$^M$—, wherein R$^M$ is selected from the group consisting of $C_{1-10}$ alkylene, $C_{2-10}$ alkenylene and $C_{2-10}$ alkynylene, and wherein the alkylene, alkenylene, alkynylene, cycloalkylene, cycloalkenylene, heteroalkylene, heteroalkenylene, heteroalkynylene, arylene and heteroarylene groups may be optionally substituted with one or more R$^N$, wherein each R$^N$ is independently selected from the group consisting of —H, —OH, —CN, —NO$_2$, —CF$_3$, —OCF$_3$, —CO$_2$H, —NH$_2$, $C_1$-$C_{10}$ alkyl, $C_2$-$C_{10}$ alkenyl, $C_2$-$C_{10}$ alkynyl, —O($C_1$-$C_{10}$ alkyl), —O($C_2$-$C_{10}$ alkenyl), —O($C_2$-$C_{10}$ alkynyl), halogen, —C(O)H, —C(O)—($C_1$-$C_{10}$ alkyl), —C(O)—O($C_1$-$C_{10}$ alkyl), —NH($C_1$-$C_{10}$ alkyl), —N($C_1$-$C_{10}$ alkyl)$_2$, —C(O)—NH($C_1$-$C_{10}$ alkyl), —C(O)—N($C_1$-$C_{10}$ alkyl)$_2$, —NH—C(O)—($C_1$-$C_{10}$ alkyl), —NH($C_1$-$C_{10}$ alkyl)-C(O)—($C_1$-$C_{10}$ alkyl), —NH—S(O)$_2$—($C_1$-$C_{10}$ alkyl), —NH—($C_1$-$C_{10}$ alkyl)-S(O)$_2$—($C_1$-$C_{10}$ alkyl), —(C$_0$-C$_{10}$)—SH, —S(O)—($C_1$-$C_{10}$ alkyl), —S(O)$_2$—($C_1$-$C_{10}$ alkyl), —S(O)$_2$—NH$_2$, —S(O)$_2$—NH—($C_1$-$C_{10}$ alkyl), —S(O)$_2$—N($C_1$-$C_{10}$ alkyl)$_2$ and =O, and c is an integer from 1 to 4, wherein if Z is directly bonded to an O or N atom, z is 0 and otherwise z is 1;
group (IID) has the formula:

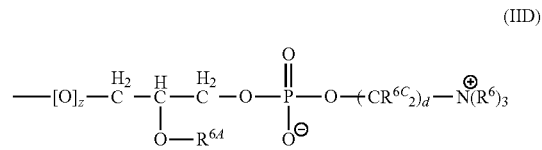

(IID)

wherein each $R^6$ and $R^{6C}$ is independently selected from hydrogen and $C_{1-4}$ alkyl; $R^{6A}$ is hydrogen or a group —C(O)B$^2$R$^{6B}$, wherein R$^{6B}$ is hydrogen or methyl, B$^2$ is selected from the group consisting of a bond; $C_{1-10}$ alkylene, $C_{2-10}$ alkenylene, $C_{2-10}$ alkynylene, $C_{3-10}$ cycloalkylene, $C_{3-10}$ cycloalkenylene, $C_{1-10}$ heteroalkylene, $C_{2-10}$ heteroalkenylene, $C_{2-10}$ heteroalkynylene, arylene, heteroarylene, —C(O)R$^M$—, —C(O)OR$^M$—, wherein R$^M$ is selected from the group consisting of $C_{1-10}$ alkylene, $C_{2-10}$ alkenylene and $C_{2-10}$ alkynylene, and wherein the alkylene, alkenylene, alkynylene, cycloalkylene, cycloalkenylene, heteroalkylene, heteroalkenylene, heteroalkynylene, arylene and heteroarylene groups may be optionally substituted with one or more R$^N$, wherein each R$^N$ is independently selected from the group consisting of —H, —OH, —CN, —NO$_2$, —CF$_3$, —OCF$_3$, —CO$_2$H, —NH$_2$, $C_1$-$C_{10}$ alkyl, $C_2$-$C_{10}$ alkenyl, $C_2$-$C_{10}$ alkynyl, —O($C_1$-$C_{10}$ alkyl), —O($C_2$-$C_{10}$ alkenyl), —O($C_2$-$C_{10}$ alkynyl), halogen, —C(O)H, —C(O)—(C$_1$-C$_{10}$ alkyl), —C(O)—O(C$_1$-C$_{10}$ alkyl), —NH(C$_1$-C$_{10}$ alkyl), —N(C$_1$-C$_{10}$ alkyl)$_2$, —C(O)—NH(C$_1$-C$_{10}$ alkyl), —C(O)—N(C$_1$-C$_{10}$ alkyl)$_2$, —NH—C(O)—(C$_1$-C$_{10}$ alkyl), —NH(C$_1$-C$_{10}$ alkyl)-C(O)—(C$_1$-C$_{10}$ alkyl), —NH—S(O)$_2$—(C$_1$-C$_{10}$ alkyl), —NH—(C$_1$-C$_{10}$ alkyl)-S(O)$_2$—(C$_1$-C$_{10}$ alkyl), —(C$_0$-C$_{10}$)—SH, —S(O)—(C$_1$-C$_{10}$ alkyl), —S(O)$_2$—(C$_1$-C$_{10}$ alkyl), —S(O)$_2$—NH$_2$, —S(O)$_2$—NH—(C$_1$-C$_{10}$ alkyl), —S(O)$_2$—N(C$_1$-C$_{10}$ alkyl)$_2$ and =O, and d is an integer from 1 to 4, wherein if Z is directly bonded to an O or N atom, z is 0 and otherwise z is 1;

group (IIE) has the formula:

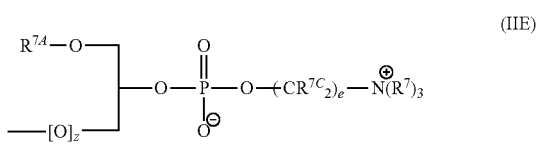

(IIE)

wherein each R$^7$ and R$^{7C}$ is independently selected from hydrogen and C$_{1-4}$ alkyl; R$^{7A}$ is hydrogen or a group —C(O)B$^2$R$^{7B}$, wherein R$^{7B}$ is hydrogen or methyl, B$^2$ is selected from the group consisting of a bond; C$_{1-10}$ alkylene, C$_{2-10}$ alkenylene, C$_{2-10}$ alkynylene, C$_{3-10}$ cycloalkylene, C$_{3-10}$ cycloalkenylene, C$_{1-10}$ heteroalkylene, C$_{2-10}$ heteroalkenylene, C$_{2-10}$ heteroalkynylene, arylene, heteroarylene, —C(O)R$^M$—, —C(O)OR$^M$—, wherein R$^M$ is selected from the group consisting of C$_{1-10}$ alkylene, C$_{2-10}$ alkenylene and C$_{2-10}$ alkynylene, and wherein the alkylene, alkenylene, alkynylene, cycloalkylene, cycloalkenylene, heteroalkylene, heteroalkenylene, heteroalkynylene, arylene and heteroarylene groups may be optionally substituted with one or more R$^N$, wherein each R$^N$ is independently selected from the group consisting of —H, —OH, —CN, —NO$_2$, —CF$_3$, —OCF$_3$, —CO$_2$H, —NH$_2$, C$_1$-C$_{10}$ alkyl, C$_2$-C$_{10}$ alkenyl, C$_2$-C$_{10}$ alkynyl, —O(C$_1$-C$_{10}$ alkyl), —O(C$_2$-C$_{10}$ alkenyl), —O(C$_2$-C$_{10}$ alkynyl), halogen, —C(O)H, —C(O)—(C$_1$-C$_{10}$ alkyl), —C(O)—O(C$_1$-C$_{10}$ alkyl), —NH(C$_1$-C$_{10}$ alkyl), —N(C$_1$-C$_{10}$ alkyl)$_2$, —C(O)—NH(C$_1$-C$_{10}$ alkyl), —C(O)—N(C$_1$-C$_{10}$ alkyl)$_2$, —NH—C(O)—(C$_1$-C$_{10}$ alkyl), —NH(C$_1$-C$_{10}$ alkyl)-C(O)—(C$_1$-C$_{10}$ alkyl), —NH—S(O)$_2$—(C$_1$-C$_{10}$ alkyl), —NH—(C$_1$-C$_{10}$ alkyl)-S(O)$_2$—(C$_1$-C$_{10}$ alkyl), —(C$_0$-C$_{10}$)—SH, —S(O)—(C$_1$-C$_{10}$ alkyl), —S(O)$_2$—(C$_1$-C$_{10}$ alkyl), —S(O)$_2$—NH$_2$, —S(O)$_2$—NH—(C$_1$-C$_{10}$ alkyl), —S(O)$_2$—N(C$_1$-C$_{10}$ alkyl)$_2$ and =O, and e is an integer from 1 to 4, wherein if Z is directly bonded to an O or N atom, z is 0 and otherwise z is 1;

each R$^1$ is independently selected from H, halogen or C$_{1-4}$ alkyl;

m is an integer from 0 to 6; and

X is NR$^2$;

where R$^2$, Y and the N atom to which they are bonded taken together form a 5 to 7 membered heterocyclic ring, wherein the heterocyclic ring may be optionally substituted with one or more R$^N$, wherein each R$^N$ is independently selected from the group consisting of —H, —OH, —CN, —NO$_2$, —CF$_3$, —OCF$_3$, —CO$_2$H, —NH$_2$, C$_1$-C$_{10}$ alkyl, C$_2$-C$_{10}$ alkenyl, C$_2$-C$_{10}$ alkynyl, —O(C)—(C$_1$-C$_{10}$ alkyl), —O(C$_2$-C$_{10}$ alkenyl), —O(C$_2$-C$_{10}$ alkynyl), halogen, —C(O)H, —C(O)—(C$_1$-C$_{10}$ alkyl), —C(O)—O(C$_1$-C$_{10}$ alkyl), —NH(C$_1$-C$_{10}$ alkyl), —N(C$_1$-C$_{10}$ alkyl)$_2$, —C(O)—NH(C$_1$-C$_{10}$ alkyl), —C(O)—N(C$_1$-C$_{10}$ alkyl)$_2$, —NH—C(O)—(C$_1$-C$_{10}$ alkyl), —NH(C$_1$-C$_{10}$ alkyl)-C(O)—(C$_1$-C$_{10}$ alkyl), —NH—S(O)$_2$—(C$_1$-C$_{10}$ alkyl), —NH—(C$_1$-C$_{10}$ alkyl)-S(O)$_2$—(C$_1$-C$_{10}$ alkyl), —(C$_0$-C$_{10}$)—SH, —S(O)—(C$_1$-C$_{10}$ alkyl), —S(O)$_2$—(C$_1$-C$_{10}$ alkyl), —S(O)$_2$—NH$_2$, —S(O)$_2$—NH—(C$_1$-C$_{10}$ alkyl), —S(O)$_2$—N(C$_1$-C$_{10}$ alkyl)$_2$ and =O;

n is an integer from 0 to 6; or

X is NR$^2$, where R$^2$ is H or C$_{1-4}$ alkyl;

Y is —C(O)O— or —C(O)N(R$^M$)—, where R$^M$ is H or C$_{1-4}$ alkyl; and n is 0; or X is O;

Y is —C(=V)A-; where V is S or O; and A is selected from NR$^M$, O and S, where

R$^M$ is hydrogen or C$_{1-4}$ alkyl; and n is 0.

2. The monomer of claim 1, wherein X is NR$^2$, and where R$^2$, Y and the N atom to which they are bonded taken together form a 5 to 7 membered heterocyclic ring, wherein the heterocyclic ring may be optionally substituted with one or more R$^N$, wherein each R$^N$ is independently selected from the group consisting of —H, —OH, —CN, —NO$_2$, —CF$_3$, —OCF$_3$, —CO$_2$H, —NH$_2$, C$_1$-C$_{10}$ alkyl, C$_2$-C$_{10}$ alkenyl, C$_2$-C$_{10}$ alkynyl, —O(C$_1$-C$_{10}$ alkyl), —O(C$_2$-C$_{10}$ alkenyl), —O(C$_2$-C$_{10}$ alkynyl), halogen, —C(O)H, —C(O)—(C$_1$-C$_{10}$ alkyl), —C(O)—O(C$_1$-C$_{10}$ alkyl), —NH(C$_1$-C$_{10}$ alkyl), —N(C$_1$-C$_{10}$ alkyl)$_2$, —C(O)—NH(C$_1$-C$_{10}$ alkyl), —C(O)—N(C$_1$-C$_{10}$ alkyl)$_2$, —NH—C(O)—(C$_1$-C$_{10}$ alkyl), —NH(C$_1$-C$_{10}$ alkyl)-C(O)—(C$_1$-C$_{10}$ alkyl), —NH—S(O)$_2$—(C$_1$-C$_{10}$ alkyl), —NH—(C$_1$-C$_{10}$ alkyl)-S(O)$_2$—(C$_1$-C$_{10}$ alkyl), —(C$_0$-C$_{10}$)—SH, —S(O)—(C$_1$-C$_{10}$ alkyl), —S(O)$_2$—(C$_1$-C$_{10}$ alkyl), —S(O)$_2$—NH$_2$, —S(O)$_2$—NH—(C$_1$-C$_{10}$ alkyl), —S(O)$_2$—N(C$_1$-C$_{10}$ alkyl)$_2$ and =O.

3. The monomer of claim 2, wherein R$^2$, Y and the N atom to which they are bonded taken together form a 5-membered heterocyclic ring.

4. The monomer of claim 3, wherein the 5-membered heterocyclic ring is substituted with =O.

5. The monomer of claim 4, which has the formula (IA):

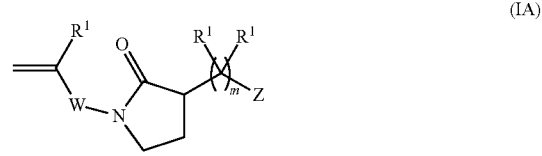

(IA)

wherein W, R$^1$, and Z as defined for formula (I).

6. The monomer of claim 5, wherein n is 0.

7. The monomer of claim 1, wherein X is NR$^2$ where R$^2$ is H or C$_{1-4}$ alkyl; Y is —C(O)O—; n is 0; and m is 1 to 4.

8. The monomer of claim 7, wherein m is 2.

9. The monomer of claim 1, wherein m is 0.

10. The monomer of claim 1, wherein Z is a group (IIB).

11. The monomer of claim 10, wherein R$^4$ is methyl and b is 2.

12. The monomer of claim 1, wherein n is 0.

13. The monomer of claim 4, wherein n is 0; m is 2; and Z is a group of formula (IIB), wherein each R$^4$ is methyl and b is 2.

14. The monomer of claim 1 of formula (ID):

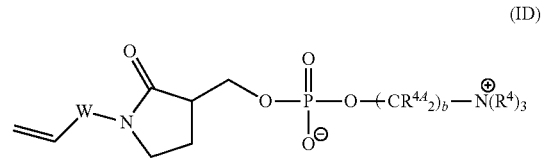

(ID)

wherein W is as defined in connection with formula (I), each R$^4$ and R$^{4A}$ is independently selected from hydrogen and C$_{1-4}$ alkyl and b is an integer from 1 to 4.

15. The monomer of claim 1, which has formula (IE):
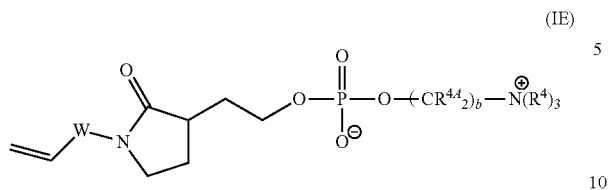
(IE)
wherein W is as defined in connection with formula (I), each $R^4$ and $R^{4A}$ is independently selected from hydrogen and $C_{1-4}$ alkyl and b is an integer from 1 to 4.
16. The monomer of claim 1 wherein X is O; Y is —C(=V)A-; where V is S or O; and A is selected from $NR^M$, O and S, where $R^M$ is hydrogen or $C_{1-4}$ alkyl; and n is 0.
* * * * *

UNITED STATES PATENT AND TRADEMARK OFFICE
CERTIFICATE OF CORRECTION

PATENT NO. : 9,006,305 B2  
APPLICATION NO. : 13/601123  
DATED : April 14, 2015  
INVENTOR(S) : Driver et al.

Page 1 of 1

It is certified that error appears in the above-identified patent and that said Letters Patent is hereby corrected as shown below:

In the claims

In Claim 1, Col. 48, Line 52, immediately after "a group" and immediately before ", wherein $R^{6B}$" please delete "-C(0)B$^2$R$^{6B}$" and insert -- -C(O)B$^2$R$^{6B}$ -- therefor.

In Claim 1, Col. 49, Line 60, immediately after "$C_2$-$C_{10}$ alkynyl," and immediately before ", -O($C_2$-$C_{10}$ alkenyl)" please delete "-O(C)-($C_1$-$C_{10}$ alkyl)" and insert -- -O($C_1$-$C_{10}$ alkyl) -- therefor.

Signed and Sealed this  
Thirteenth Day of October, 2015

Michelle K. Lee  
*Director of the United States Patent and Trademark Office*